US010279122B2

(12) United States Patent
Jakob et al.

(10) Patent No.: US 10,279,122 B2
(45) Date of Patent: May 7, 2019

(54) MEDICAL INJECTION DEVICE

(71) Applicant: Raumedic AG, Helmbrechts (DE)

(72) Inventors: Thomas Jakob, Selb (DE); Sebastian Maag, Bayreuth (DE); Tobias Festel, Sparneck (DE); Thomas Braun, Hof (DE); Frank Skaper, Leupoldsgrün (DE)

(73) Assignee: Raumedic AG, Münchberg (DE)

( * ) Notice: Subject to any disclaimer, the term of this patent is extended or adjusted under 35 U.S.C. 154(b) by 1041 days.

(21) Appl. No.: 14/339,828

(22) Filed: Jul. 24, 2014

(65) Prior Publication Data
US 2015/0032062 A1 Jan. 29, 2015

(30) Foreign Application Priority Data

Jul. 24, 2013 (DE) ........................ 10 2013 214 442

(51) Int. Cl.
*A61M 5/32* (2006.01)
*A61M 5/31* (2006.01)
(52) U.S. Cl.
CPC .......... *A61M 5/326* (2013.01); *A61M 5/3202* (2013.01); *A61M 5/3216* (2013.01); *A61M 5/3245* (2013.01); *A61M 2005/312* (2013.01); *A61M 2005/3118* (2013.01); *A61M 2005/3217* (2013.01)

(58) Field of Classification Search
CPC .............. A61M 5/3243; A61M 5/3245; A61M 5/3257; A61M 5/3271; A61M 5/3275; A61M 5/344; A61M 5/345; A61M 5/348; A61M 2005/3247; A61M 2005/3253; A61M 2005/3258

See application file for complete search history.

(56) References Cited

U.S. PATENT DOCUMENTS

| 4,720,285 | A | | 1/1988 | Pickhard | |
|---|---|---|---|---|---|
| 4,804,372 | A | * | 2/1989 | Laico | .................. A61M 5/3243 604/198 |
| 4,838,871 | A | | 6/1989 | Luther | |
| 4,874,384 | A | * | 10/1989 | Nunez | ................. A61M 5/3243 128/919 |
| 4,894,055 | A | * | 1/1990 | Sudnak | ............... A61M 5/3271 604/110 |
| 4,897,083 | A | * | 1/1990 | Martell | ............... A61M 5/3202 604/192 |

(Continued)

FOREIGN PATENT DOCUMENTS

| CH | 685979 | 11/1995 |
|---|---|---|
| DE | 695 02 357 | 1/1999 |

(Continued)

*Primary Examiner* — Kami A Bosworth
(74) *Attorney, Agent, or Firm* — Boyle Fredrickson S.C.

(57) ABSTRACT

A medical injection device has an injection unit and an anti-rotation device. Said anti-rotation device is non-rotationally connected to a port and connection portion of the injection device so as to surround the outside thereof in the manner of a sleeve. As a result, an intuitively usable and operationally safe injection device is obtained. When a protective cap for an injection cannula of the injection unit is being removed from the port and connection portion, an unwanted rotation of the port and connection portion relative to the container about components of a plug-in connection arranged therebetween is safely prevented.

8 Claims, 21 Drawing Sheets

(56) References Cited

U.S. PATENT DOCUMENTS

| | | | |
|---|---|---|---|
| 4,927,416 A * | 5/1990 | Tomkiel | A61M 5/315 604/198 |
| 4,944,397 A | 7/1990 | Miller | |
| 4,982,842 A | 1/1991 | Hollister | |
| 5,139,489 A | 8/1992 | Hollister | |
| 5,154,285 A | 10/1992 | Hollister | |
| 5,232,454 A | 8/1993 | Hollister | |
| 5,232,455 A | 8/1993 | Hollister | |
| 5,242,416 A * | 9/1993 | Hutson | A61M 5/3216 604/192 |
| 5,267,977 A * | 12/1993 | Feeney, Jr. | A61M 5/3271 604/198 |
| 5,277,311 A | 1/1994 | Hollister | |
| 5,295,975 A * | 3/1994 | Lockwood, Jr. | A61M 5/3243 604/198 |
| 5,312,367 A | 5/1994 | Nathan | |
| 5,342,322 A | 8/1994 | Nathan et al. | |
| 5,423,765 A | 6/1995 | Hollister | |
| 5,584,816 A | 12/1996 | Gyure et al. | |
| 5,632,732 A | 5/1997 | Szabo et al. | |
| 5,643,219 A | 7/1997 | Burns | |
| 5,897,224 A * | 4/1999 | Freund | G03B 17/08 396/25 |
| 7,850,661 B2 * | 12/2010 | Chevallier | A61M 5/326 604/198 |
| 2004/0102740 A1 * | 5/2004 | Meloul | A61M 5/3257 604/263 |
| 2005/0067023 A1 * | 3/2005 | Palvolgyi | F02M 37/0023 137/538 |
| 2008/0177237 A1 * | 7/2008 | Stonehouse | A61M 5/326 604/263 |
| 2009/0287158 A1 * | 11/2009 | Hund | A61M 5/3202 604/192 |
| 2009/0299295 A1 * | 12/2009 | Rubinstein | A61M 5/326 604/198 |
| 2010/0008768 A1 * | 1/2010 | Vedsted | F04D 7/04 415/173.1 |
| 2012/0029481 A1 * | 2/2012 | Pech | A61M 39/10 604/533 |
| 2013/0267910 A1 * | 10/2013 | Hemmann | A61M 5/326 604/198 |

FOREIGN PATENT DOCUMENTS

| | | |
|---|---|---|
| DE | 60032171 | 10/2007 |
| EP | 0 460 914 | 11/1995 |
| EP | 0 692 271 | 4/2002 |
| EP | 0 707 860 | 12/2002 |
| EP | 0 885 621 | 12/2002 |
| EP | 0 862 920 | 1/2003 |
| EP | 1 568 321 | 8/2005 |
| EP | 1 790 367 A | 5/2007 |
| EP | 1 587 419 | 11/2009 |
| EP | 1 592 346 | 7/2011 |
| EP | 1 525 016 | 11/2011 |
| WO | 91/09639 | 7/1991 |
| WO | 2004103431 A2 | 12/2004 |

* cited by examiner

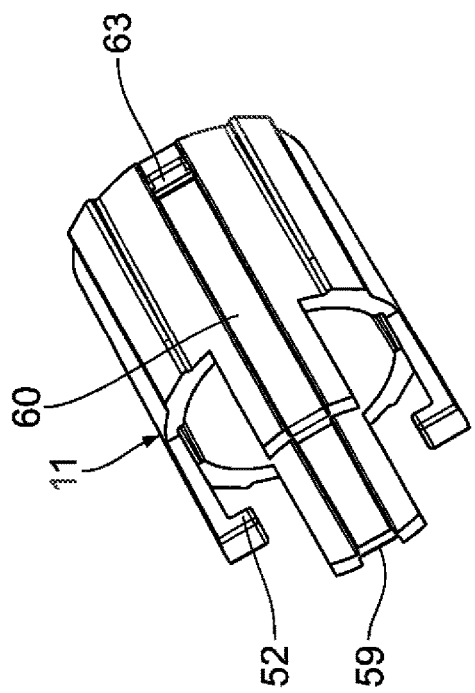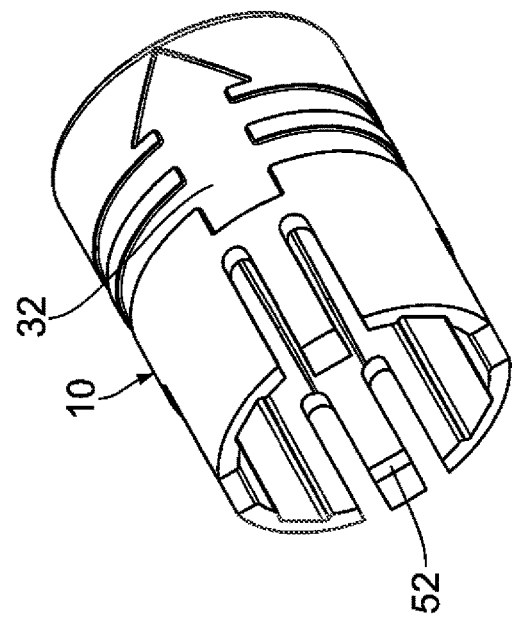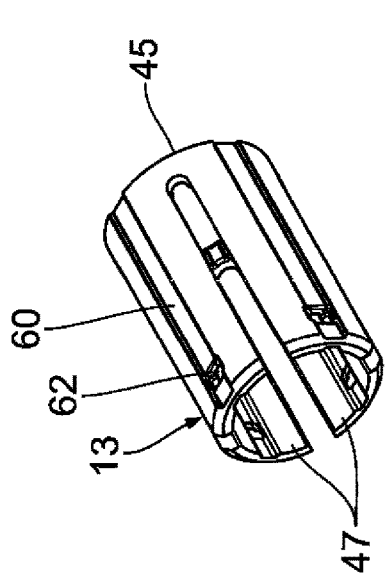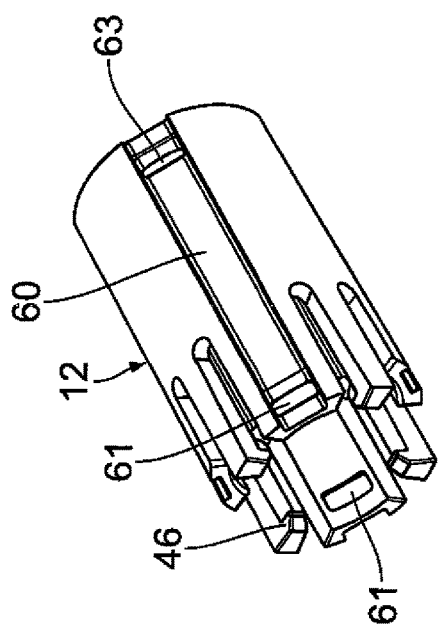

MEDICAL INJECTION DEVICE

CROSS-REFERENCE TO RELATED APPLICATIONS

This application claims the priority of German patent application, Serial No. DE 10 2013 214 442.3, filed Jul. 24, 2013, pursuant to 35 U.S.C. 119(a)-(d), the content of which is incorporated herein by reference in its entirety as if fully set forth herein.

FIELD OF THE INVENTION

The invention relates to a medical injection device comprising an injection unit.

BACKGROUND OF THE INVENTION

Medical injection devices are known from EP 460 914 B1, from EP 707 860 B1, from U.S. Pat. No. 4,838,871, from EP 692 271 B1, from U.S. Pat. No. 4,944,397, from U.S. Pat. No. 4,982,842, from U.S. Pat. No. 5,232,455, from U.S. Pat. No. 5,139,489, from U.S. Pat. No. 5,154,285, from U.S. Pat. No. 5,277,311, from U.S. Pat. No. 5,232,454, from U.S. Pat. No. 5,312,367, from U.S. Pat. No. 5,342,322, from U.S. Pat. No. 5,423,765, from U.S. Pat. No. 5,643,219, from WO 1991/009639 A2, from EP 862 920 B1, from EP 885 621 B1, from EP 1 525 016 B1, from EP 1 568 321 A1, from EP 1 587 419 B1, from EP 1 592 346 B1, from U.S. Pat. No. 5,584,816 and from U.S. Pat. No. 5,632,732. An injection syringe comprising a needle sheath is known from DE 600 32 171 T2.

SUMMARY OF THE INVENTION

It is an object of the present invention to further develop an injection device of the type named at the outset in such a way that an intuitively usable and operationally safe injection device is obtained.

According to the invention, this object is achieved by a medical injection device comprising an anti-rotation device which is non-rotationally connected to the port and connection portion, and which surrounds the outside of the port and connection portion in the manner of a sleeve.

In order to remove the protective cap from the injection cannula, a user may either grasp the anti-rotation device or the protective cap. When the protective cap is being screwed off in order to remove the protective cap from the port and connection portion, an unwanted rotation of the container relative to the port and connection portion in the region of the plug-in connection is then not possible. This prevents an unwanted release of the plug-in connection when the protective cap is being screwed off, thus ensuring that an interior of the container remains sterile. The plug-in connection may be a tapered connection. The plug-in connection may be a Luer-Lock connection. The plug-in connection may be configured in a rotationally-symmetric manner in such a way as to allow for a rotation of the port and connection portion relative to the near-cannula end of the container about a cannula axis. The plug-in connection may be provided with at least one snap-in portion such that the connection is secured by means of a positive fit.

An axial covering of the plug-in connection by the anti-rotation protection prevents access to the plug-in connection from outside, which also helps to prevent an unwanted release of the plug-in connection.

A positive-fit adapter between the anti-rotation device and the injection unit ensures a rotation-proof connection of the anti-rotation device and the injection unit. The positive-fit adapter is also connected to the remaining anti-rotation device in a rotation-proof manner. The positive-fit adapter may be a component of the anti-rotation device.

This applies in particular to a positive-fit adapter that is non-rotationally connected to the port and connection portion via a positive-fit connection.

A configuration of the anti-rotation device comprising at least one positive-fit latch that is received between two adjacent, axially extending peripheral ribs of the port and connection portion, wherein the positive-fit latches are held between the peripheral ribs by means of at least one hold-down means provides for a particularly secure anti-rotation protection of the positive-fit adapter relative to the port and connection portion. The hold-down means may be formed by a hold-down sleeve, for example a telescopic sleeve, which is push-fitted over the positive-fit adapter during an assembly of the anti-rotation device. The hold-down means ensures that the at least one positive-fit latch is non-rotationally connected to the port and connection portion. The remaining anti-rotation device may be rigidly connected to the at least one positive-fit latch. There may be provided a plurality of positive-fit latches which surround an axial longitudinal axis of the port and connection portion and therefore the entire injection unit. A number of the positive-fit latches may be adapted to a width and a number of peripheral ribs of the port and connection portion.

A carrier ring configuration of the positive-fit adapter formed in one piece with the at least one positive-fit latch, wherein the carrier ring is push-fittable onto the port and connection portion and is snap-locked therewith, results in a particularly stable design and an effective anti-rotation protection. Alternatively, the positive-fit adapter may be configured in the shape of a letter C such that it is push-fittable over the port and connection portion from the side and is in particular snap-lockable therewith. This facilitates an assembly of the positive-fit adapter.

An embodiment for holding down the at least one positive-fit latch by means of at least one inner axial rib which interacts with a counter hold-down means at the positive-fit adapter results in a particularly secure anti-rotation protection of the positive-fit adapter relative to the port and connection portion. The hold-down counter means may be formed by an outer axial rib of the positive-fit adapter.

A multi-component injection-molding design of the at least one component of the anti-rotation protection increases the possibilities of manufacturing the components of the anti-puncture device. The multi-component injection-molded part may be configured as a two-component injection-molded part or as an injection-molded part comprising more than two components, for instance three components, four components, five components or even more components. Softer plastic materials may be combined with harder plastic materials. Softer plastic materials may for instance be used for a grip portion of the anti-puncture device or for formed parts abutting against counter components in order to compensate for a play therebetween and/or in order to produce or increase a frictional fit between the respective formed part and the respective counter component.

A soft component of the multi-component injection-molded part may for instance be produced from one or more than one thermoplastic elastomers (TPE), from polyurethane or from silicone. A hard component of the multi-component injection-molded part may be produced from polypropylene, from polyethylene, from ABS (acrylonitrile butadiene styrene), from a thermoplastic material on the basis of methyl metacrylate, acrylonitrile, butadiene and styrene (MABS), from polyoxymethylene, from polybutylene terephthalate (PBT) or in the form of a blended system, in other words a mixture, on the basis of polyolefins as well as polyamide.

The embodiment in which the at least one multi-component injection-molded part of the anti-rotation device is configured as an outer sleeve which has at least one grip portion and at least one carrier body, wherein the carrier body on the one hand and the at least one grip portion on the other are configured as different injection-molded components of the multi-component injection-molded part is an advantageous embodiment for the use of multi-component injection-molded parts.

A multi-component injection-molding design of the positive-fit member and the positive-fit member carrier body allows the at least one positive-fit member, which may be configured as an axial rib, to be made of a material that is softer than that of the positive-fit member carrier body, with the result that a frictional fit between the positive-fit members and the inner port and connection portion is improved. This results in an improved anti-rotation protection of the positive-fit adapter relative to the port and convection portion.

Exemplary embodiments of the invention will hereinafter be explained in more detail with reference to the drawing.

BRIEF DESCRIPTION OF THE DRAWING

FIGS. 36 to 42 show illustrations, similar to FIGS. 18 to 24, of components of another embodiment of an anti-puncture device for an injection unit.

DESCRIPTION OF THE PREFERRED EMBODIMENTS

Figure 1:
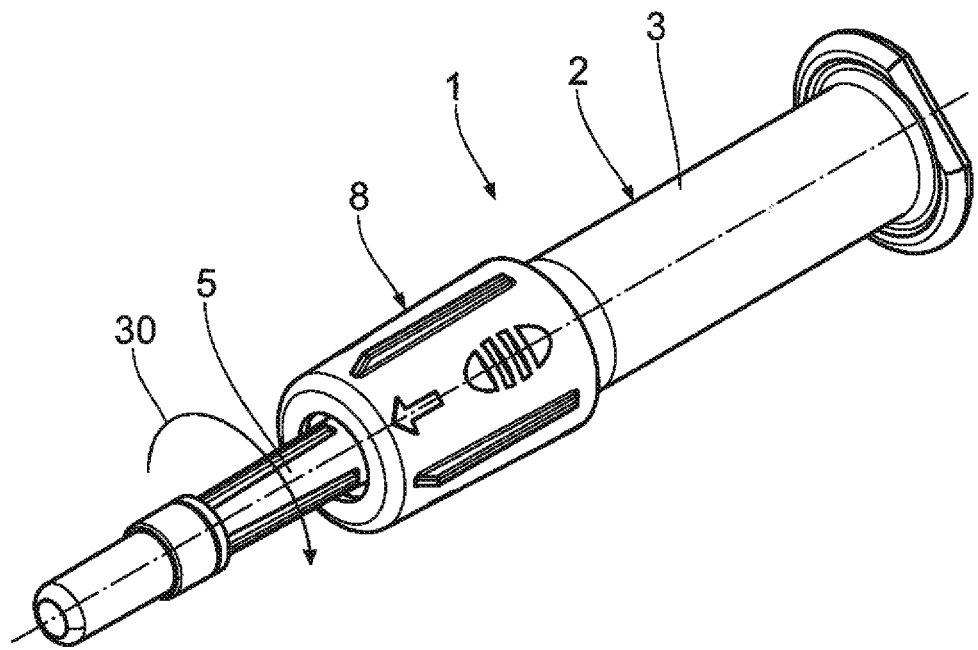
FIG. 1 shows a medical injection device, assembled and ready for delivery, comprising an injection unit and a telescopic anti-puncture device.

FIGS. 1 to 11 show an embodiment of a medical injection device 1. The injection device 1 has an injection unit 2. This injection unit 2 includes a container 3 for the medium to be injected. The container 3 may be configured as a syringe container for receiving a syringe plunger which is not shown in the drawing. The injection unit 2 further includes an injection cannula 4 which is visible in FIG. 2 and which is covered in FIG. 1 by an original protective cap 5. Upon delivery of the injection device 1 according to FIG. 1, the original protective cap 5 is fitted onto the injection cannula 4 and axially snap-locked with a near-cannula end of the container 3. For injection of the medium, the injection cannula 4 communicates with the container 3 via a near-cannula port and connection portion 6 of the container 3 which is visible in the sectional view according to FIG. 5. The port and connection portion 6 is also referred to as opening and connection portion 6. The opening and connection portion 6 is push-fitted onto a conically tapering opening end of a glass body of the container 3 and may additionally be connected therewith by means of a positive-fit connection, in particular a snap-in locking connection. The injection cannula 4, which is a cannula made of metal, is connected to the opening portion 6 via a plug-in connection, in other words a tapered connection 7. In an embodiment of the injection device 1 not shown, the tapered connection 7 is configured as a Luer-Lock connection. In the region of the plug-in connection, in other words the tapered connection 7, an inner wall of the opening portion 6 may be snap-locked with an outer wall of a cannula projection or may be positively connected therewith in any other way.

Apart from the injection cannula 4, all components of the injection device 1 are made of plastics. It is however conceivable for the injection cannula 4 to be made of plastics as well.

The injection device 1 is further provided with an anti-puncture device 8. Said anti-puncture device 8 is displaceable between an injection position shown in FIG. 2 in which the injection cannula 4 is exposable for instance for subcutaneous or intravenous injection of the medium, and a protection position shown in FIG. 4 in which a cannula tip 9 of the injection cannula 4 is retracted into a protective component 10 of the anti-puncture device 8.

The anti-puncture device 8 surrounds the opening portion 6 in the form of a sleeve and has at least two telescopic sleeves. In the embodiment according to FIGS. 1 to 11, the anti-puncture device 8 has a total of three telescopic sleeves 10, 11 and 12, wherein one of these three telescopic sleeves, the telescopic protection sleeve 10, acts as the protective component of the anti-puncture device 8. At the same time, the telescopic protection sleeve 10 is the outermost of the three telescopic sleeves 10 to 12 of the anti-puncture device 8. An innermost of the three telescopic sleeves, the telescopic connection sleeve 12, is connected to the injection unit 2 via a positive-fit adapter 13. The telescopic sleeve 11 is arranged between the innermost telescopic sleeve 12 and the outermost telescopic sleeve 10 of the anti-puncture device 8 and forms another telescopic sleeve of the anti-puncture device 8.

In the injection position, the telescopic sleeves 10 to 12 are disposed one above the other in such a way as to be in perfect alignment. In the injection position, the anti-puncture device 8 axially covers the tapered connection 7, thus preventing access thereto from outside. In the protection position, the telescopic sleeves 10 to 12 are extended relative to each other.

Figure 5:
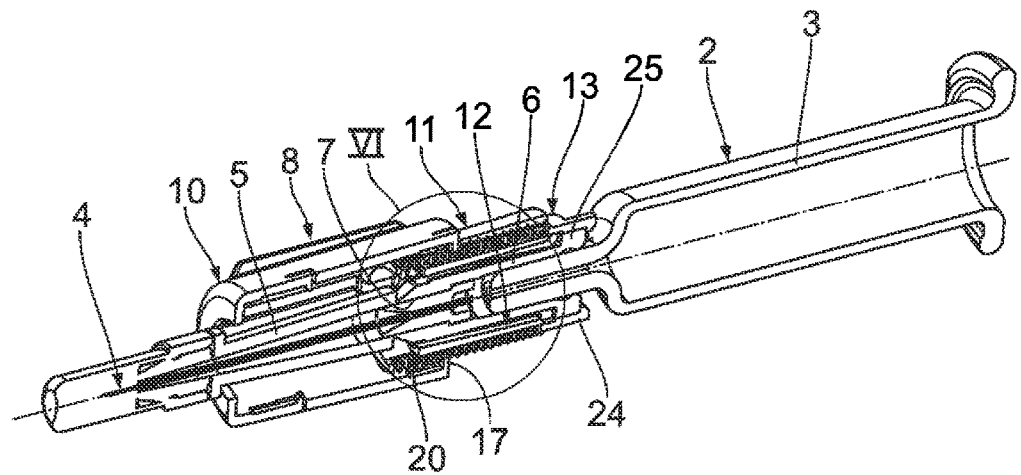
FIG. 5 shows a partial longitudinal section through the injection device with the original protective cap fitted thereto, wherein the telescopic anti-puncture device is shown in a position between the injection position and the protection position.
Figure 6:
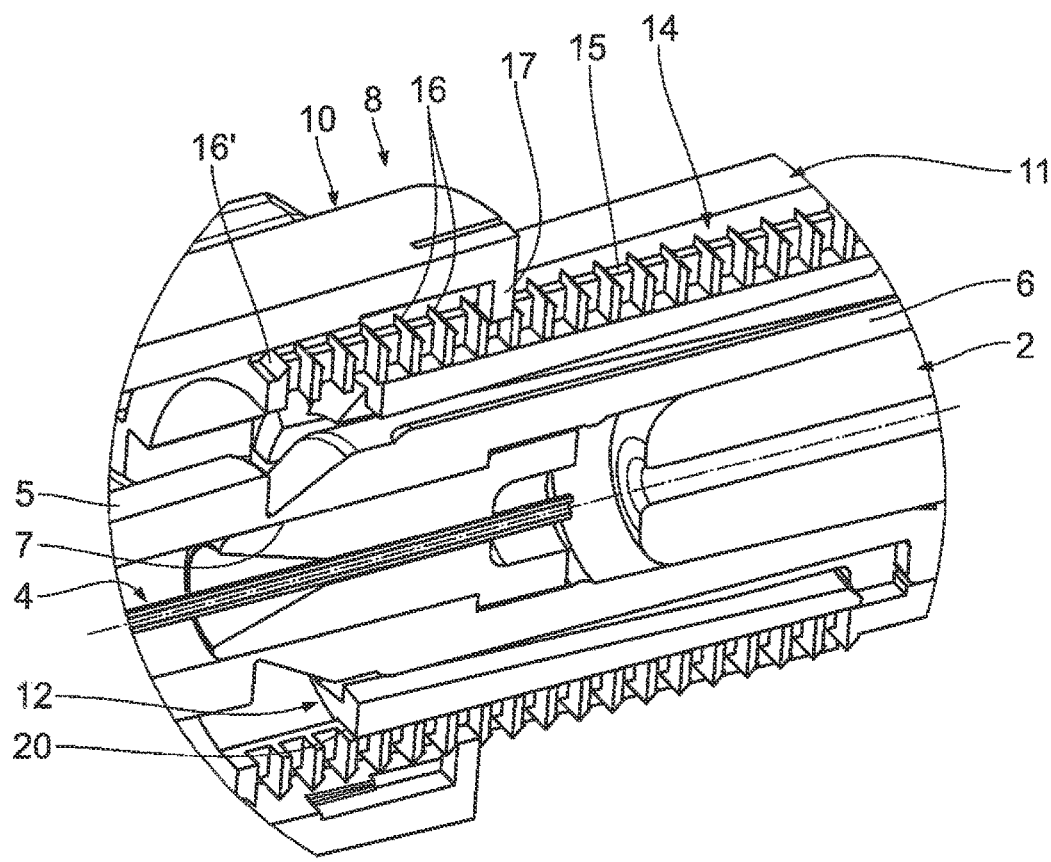
FIG. 6 shows an enlarged sectional view of detail VI in FIG. 5.

FIGS. 5 and 6 show details of the injection device 1 and in particular details of the anti-puncture device 8.

A protective unit in the form of a protective snap-in locking arrangement 14 is provided to ensure that the protective component, in other words the outermost telescopic protective cap 10, is securely fastened in the protection position. Said protective snap-in locking arrangement 14 has rows 15 of snap-in locking teeth comprising snap-in locking teeth 16 that are arranged one behind the other along the central telescopic sleeve 11 and the inner telescopic connection sleeve 12. Each of the telescopic sleeves 11, 12 has two outer rows 15 of snap-in locking teeth which are arranged opposite to each other when seen in the peripheral direction about the longitudinal axis of the injection device. The two rows 15 of snap-in locking teeth of the central telescopic sleeve 11 are staggered by 90° relative to the two rows 15 of teeth of the inner telescopic connection sleeve 12 when seen in the peripheral direction about the longitudinal axis of the injection device 1. Each of the snap-in locking teeth 16 is engaged by a counter snap-in locking body 17 of the outer telescopic protection sleeve 10 or by a counter snap-in locking body 18 (cf. FIG. 7) of the central telescopic sleeve 11. In the axial longitudinal sectional view of the injection device, the snap-in locking teeth 16 have a sawtooth profile with a preferred direction which allows the telescopic sleeves 10, 11 to be moved from the injection position into the extended protection position in one direction only. One snap-in locking tooth 16' (cf. FIG. 6), which corresponds to a maximum extended relative position of the associated telescopic sleeves 10, 11, has a preferred direction which is exactly opposite thereto when seen in the axial sectional view in order to define the maximum extended position, in other words the protection position of the anti-puncture device 8.

The snap-in locking teeth 16 are formed in one piece with the respective telescopic sleeve 11, 12.

The anti-puncture device 8 is provided with groove/tongue guide devices 19 which ensure a telescopic guidance and at the same time an anti-rotation protection between two adjacent ones of the three telescopic sleeves 10 to 12, in other words between the telescopic sleeves 10, 11 on the one hand and the telescopic sleeves 11, 12 on the other.

Figure 7:
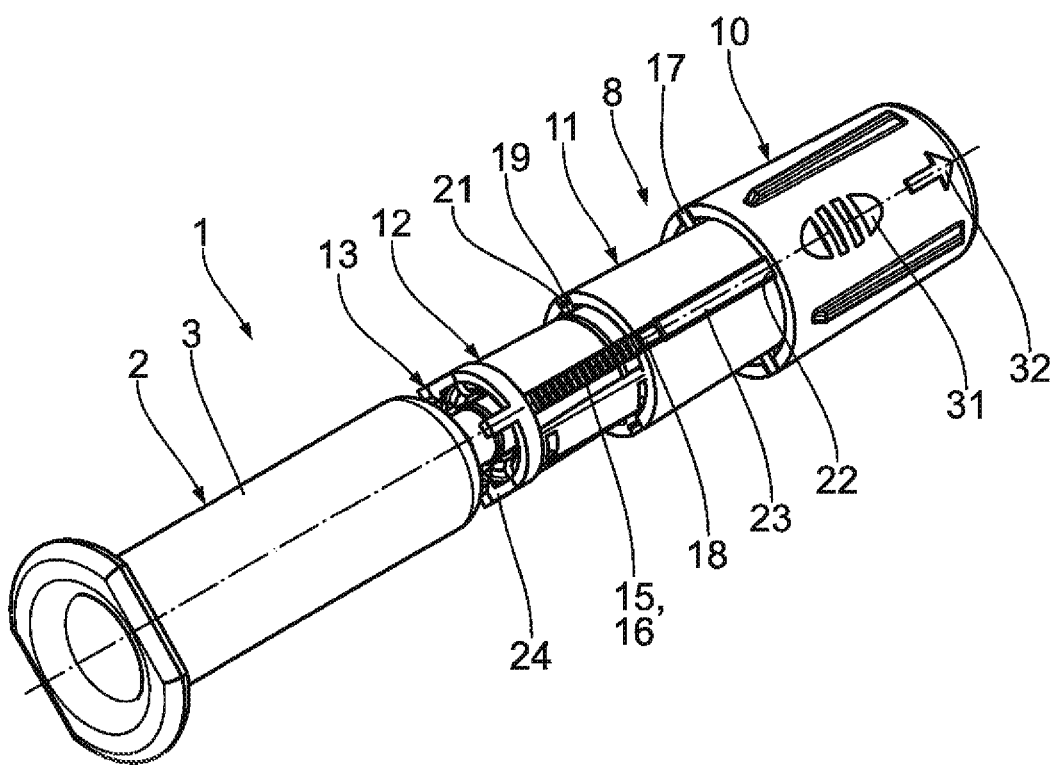
FIG. 7 shows an enlarged view of a section of the injection device in the protection position.

FIG. 7 shows a groove 20 of one of the groove/tongue guide devices 19 which is formed in an outer jacket wall of the inner telescopic connection sleeve 12 in the form of an axial longitudinal groove. This groove 20 is engaged by a complementary tongue 21 which projects inwardly from an inner wall of the central telescopic sleeve 11. The tongue 21 of the central telescopic sleeve 11, which interacts with the groove 20 of the inner telescopic sleeve 12 in a guiding manner, is formed by the inner ends of the snap-in locking teeth 16 of the central telescopic sleeve 11.

Another tongue/groove guide device 19 is formed by axial longitudinal grooves 22 in the inner jacket wall of the outer telescopic protection sleeve 10 and tongues 23 complementary thereto which are formed in the outer jacket wall of the central telescopic sleeve 11 in such a way as to radially protrude in the outward direction. Two identical groove/tongue guide devices 19 are in each case arranged opposite to each other relative to the longitudinal axis of the injection device 1. Relative to one of the telescopic sleeves 10, 12, the snap-in locking components of the snap-in locking arrangement 14 are alternately arranged with the components of the groove/tongue guide device 19 such that one snap-in locking component of the snap-in locking protective arrangement 14 is in each case followed by a component of the groove/tongue guide device 19 which is staggered thereto by 90° when seen in the peripheral direction about the longitudinal axis of the injection device 1.

FIGS. 8 to 11 show instantaneous positions during assembly of the injection device 1. The positive-fit adapter 13 is locked with the container 3 of the injection unit 2 by means of snap-in locking hooks 24. To this end, the snap-in locking hooks 24 engage a snap-in locking collar 25 of the container 3 which is arranged at the transition to the opening portion 6. The inner telescopic connection sleeve 12 is axially connected to the positive-fit adapter 13 by means of a plurality of snap-in locking bodies 26 which are formed at free ends of snap-in latches 27 of the positive-fit adapter 13. The snap-in latches 27 extend in the axial direction and are formed at a common carrier ring 28 of the positive-fit adapter 13. The positive-fit adapter 13 therefore has the shape of an axially fittable adapter sleeve. A distance between two snap-in latches 27 which are adjacent to each other when seen in the peripheral direction about the longitudinal axis of the injection device 1, and the number of the snap-in latches 27 is adapted to a width and a number of axially extending peripheral ribs 29 which are formed on an outside of the opening portion 6 of the container 3. When the positive-fit adapter 13 is mounted, a respective one of the snap-in latches 27 fits between two adjacent ones of the peripheral ribs 29, thus ensuring an anti-rotation protection of the positive-fit adapter 13 relative to the container 3, strictly speaking relative to the opening and connection portion 6 of the container 3. An inner wall of the inner telescopic connection sleeve 12 is provided with axial structures which are not shown in more detail in the drawing and which ensure an anti-rotation protection between the inner telescopic connection sleeve 12 and the positive-fit adapter 13 when the inner telescopic connection sleeve 12 is snap-locked with the positive-fit adapter 13. The inner axial structures of the telescopic connection sleeve 12 engage into the space between in each case two adjacent snap-in latches 27 of the positive-fit adapter 13.

When the inner telescopic connection sleeve 12 is mounted, the snap-in locking bodies 26 engage a complementary snap-in locking collar of the telescopic connection sleeve 12, which is not shown in more detail in the drawing.

An injection connection arrangement configured as an injection snap-in locking arrangement allows the telescopic protection sleeve 10, in other words the protective component of the anti-puncture device 8, to be positively and securely fastened to the injection unit 2 in the injection position. Snap-in locking components of said injection snap-in locking arrangement are on the one hand the outer edges of the free ends of the snap-in locking hooks 24 of the positive-fit adapter 13, and the counter snap-in locking bodies 17 of the telescopic protection sleeve 10 on the other which engage therewith in the injection position. Said injection snap-in locking arrangement 17, 24 can be released from engagement with the snap-in latches 24 by disengaging the counter snap-in locking bodies 17. This is done by applying a defined amount of pressure to the anti-puncture device 8.

Figure 8:
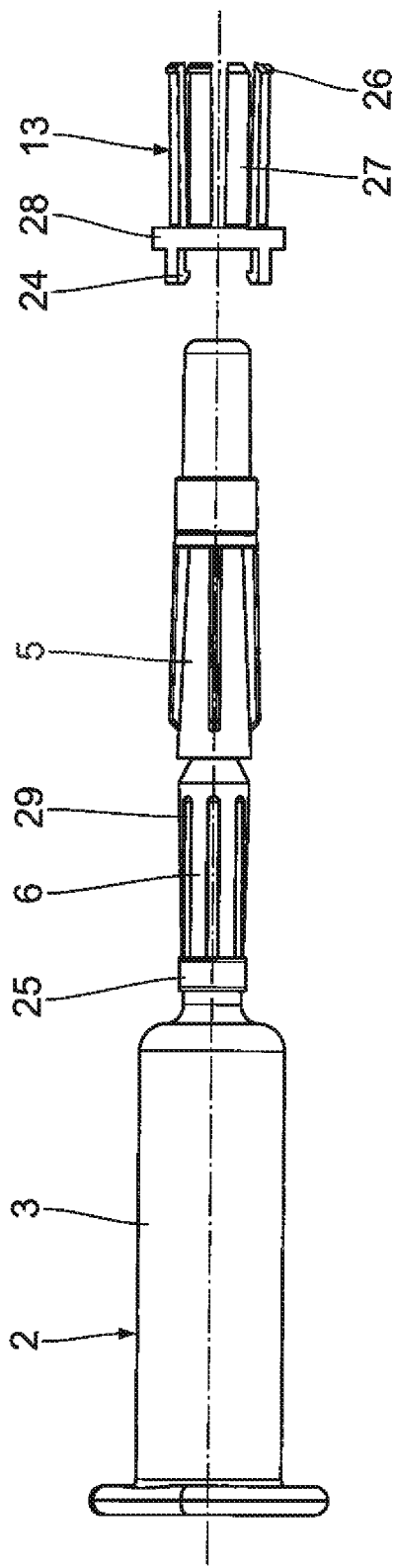
FIGS. 8 to 11 show instantaneous positions during assembly of the injection device.
Figure 9:
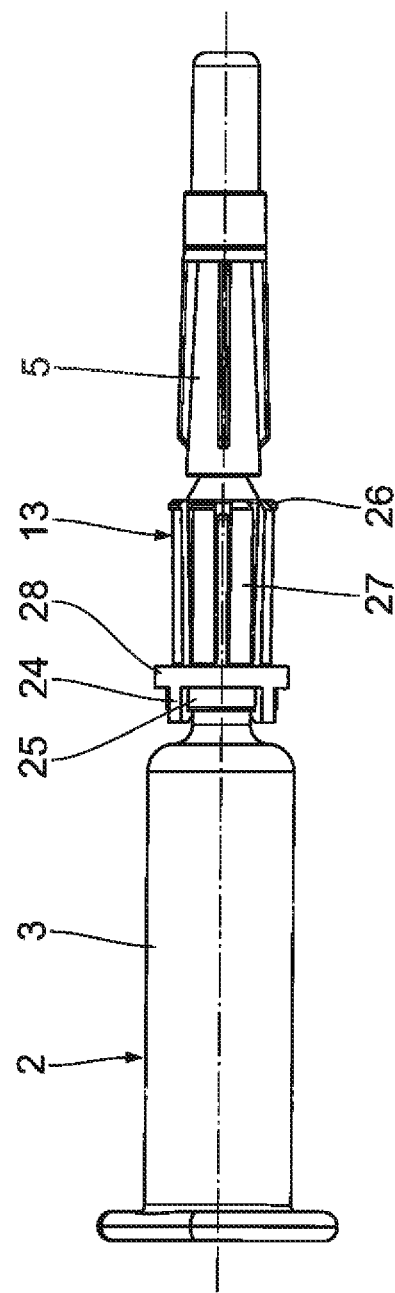
Figure 10:
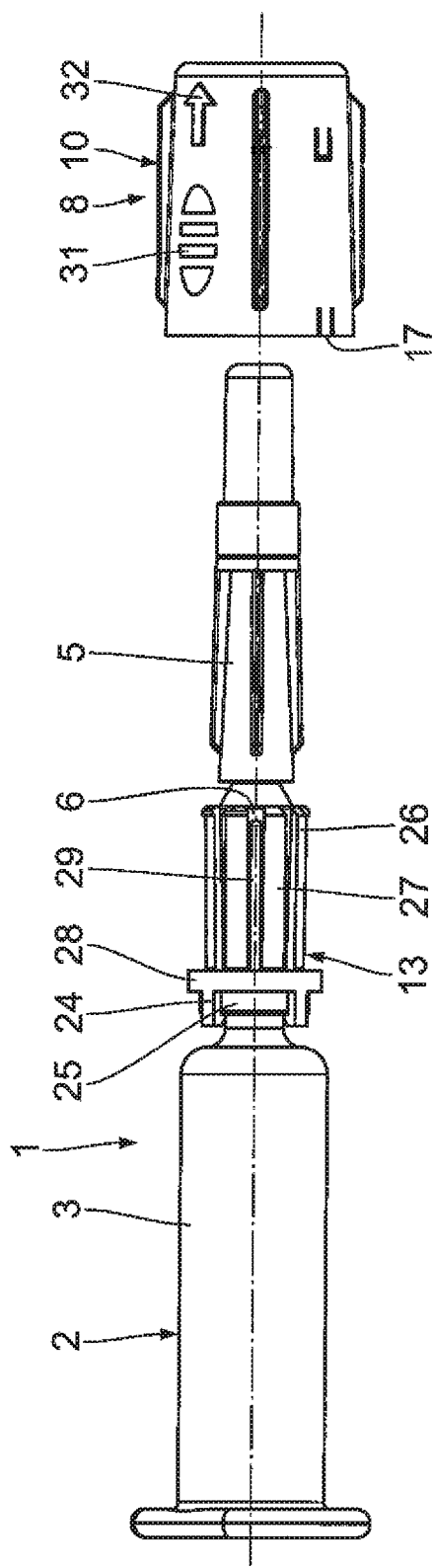

The injection device 1 is assembled as follows: At first, the injection unit 2 is in a commercially available supply condition which is shown in FIG. 8. The anti-puncture device 8 comprising the sleeves 10 to 12 is preassembled in the injection position in which the telescopic sleeves are disposed one above the other in such a way as to be in perfect alignment. The positive-fit adapter 13 is then push-fitted onto the injection unit 2 from the cannula end of the injection unit 2 with its snap-in locking hooks 24 ahead until the snap-in locking hooks 24 engage the snap-in locking collar 25 of the container 3 (cf. FIG. 9). Afterwards, the prefabricated anti-puncture device 8 comprising the three telescopic sleeves 10 to 12, which are fitted one inside the other and snap-locked with each other, is push-fitted onto the injection unit 2 from the cannula end of the injection unit 2 as well until the inner telescopic connection sleeve 12 snap-locks with the positive-fit adapter 13, causing the snap-in latches 27 to be radially pressed between the peripheral ribs 29 to achieve an anti-rotation protection, and the injection snap-in locking arrangement 17, 24 comes into locking engagement. The inner telescopic connection sleeve 12 is oriented in the peripheral direction in such a way that when it is push-fitted onto the positive-fit adapter 13, the inner axial structures of the telescopic connection sleeve 12 engage into the space between the snap-in latches 27 of the positive-fit adapter 13. When the inner telescopic connection sleeve 12 has been fully push-fitted onto the positive-fit adapter 13, a leading stop collar of the telescopic connection sleeve 12 abuts against a front wall of the carrier ring 28 of the positive-fit adapter 13 facing the stop collar.

At the same time, inner structures of the telescopic connection sleeve 12 act as hold-down means for holding the snap-in latches 27 between the peripheral ribs 29 of the opening portion 6 of the injection unit 2.

Figure 11:
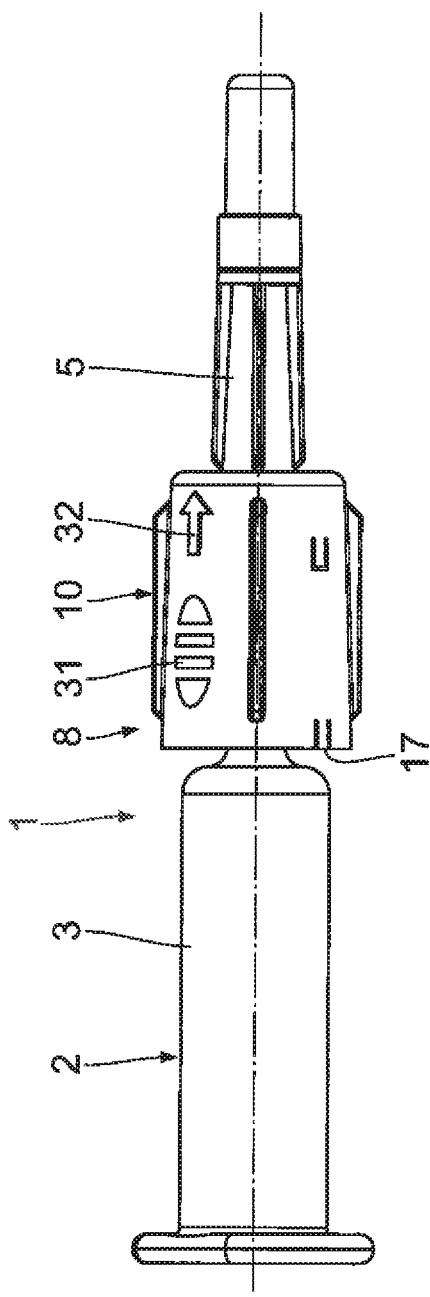
Figure 12:
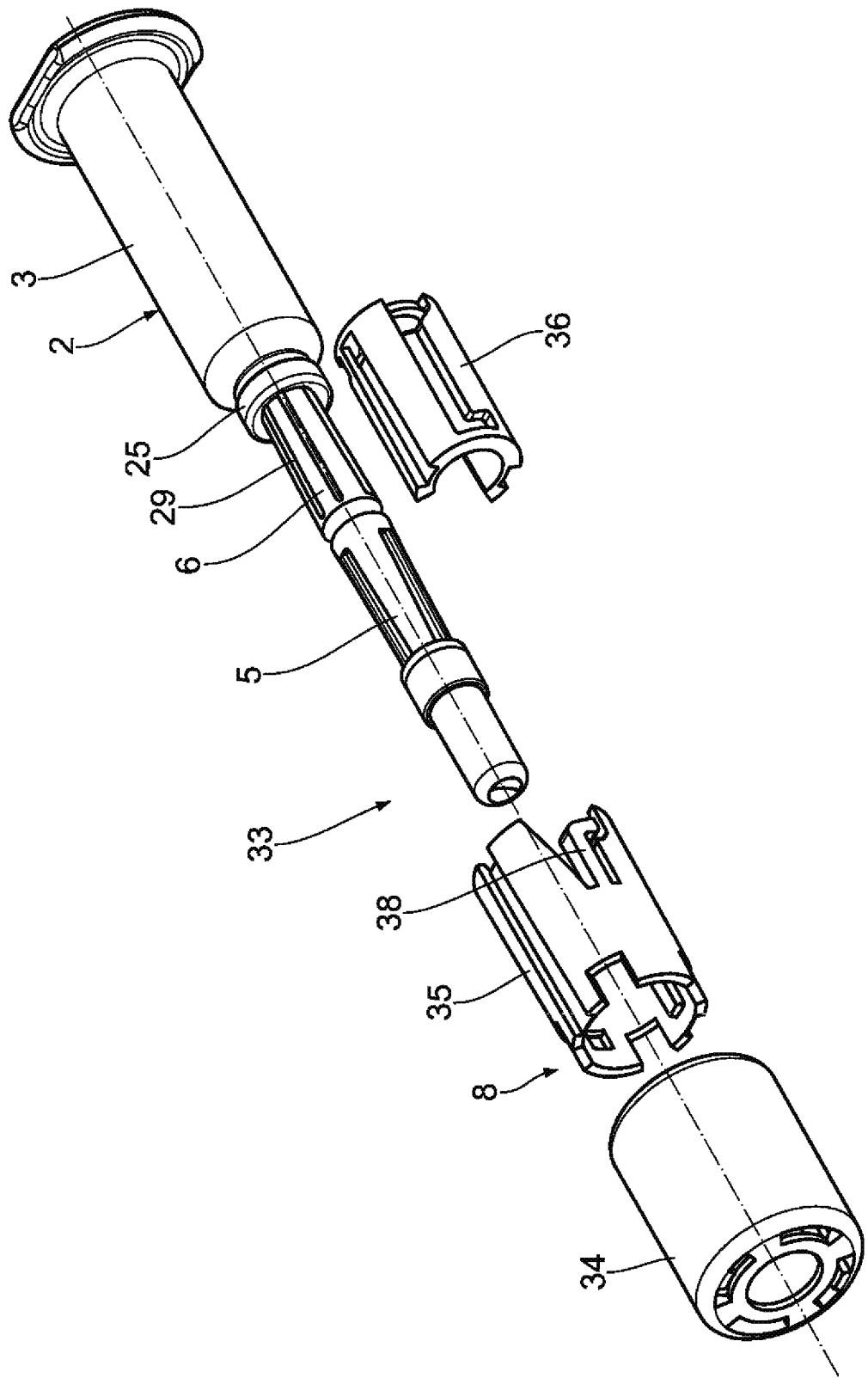
FIG. 12 shows an exploded view of another embodiment of a medical injection device comprising a telescopic anti-puncture device.
Figure 13:
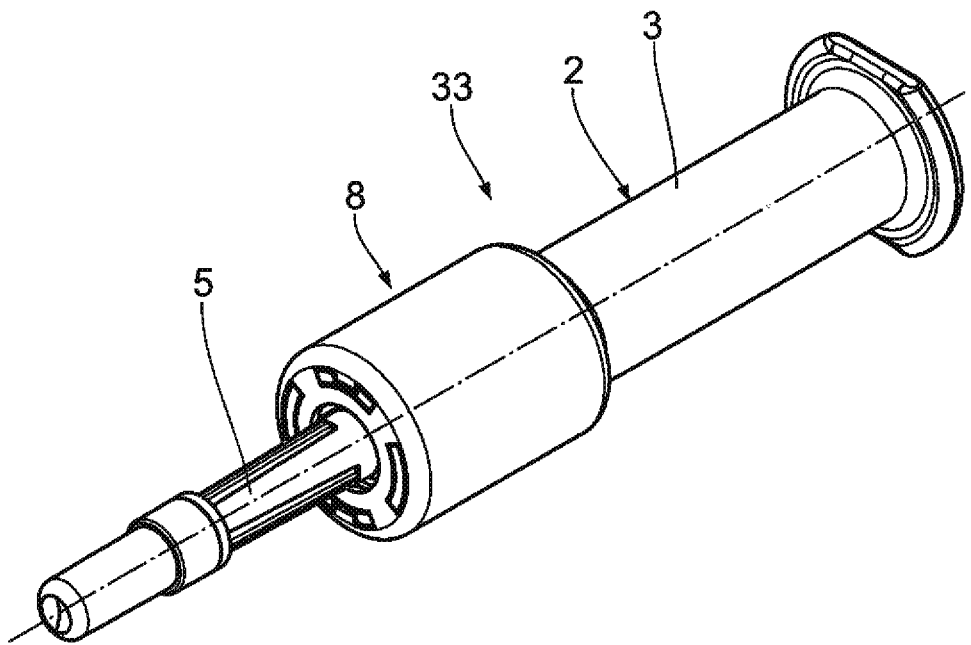
FIG. 13 shows the injection device according to FIG. 12 with its anti-puncture device in the injection position.
Figure 14:
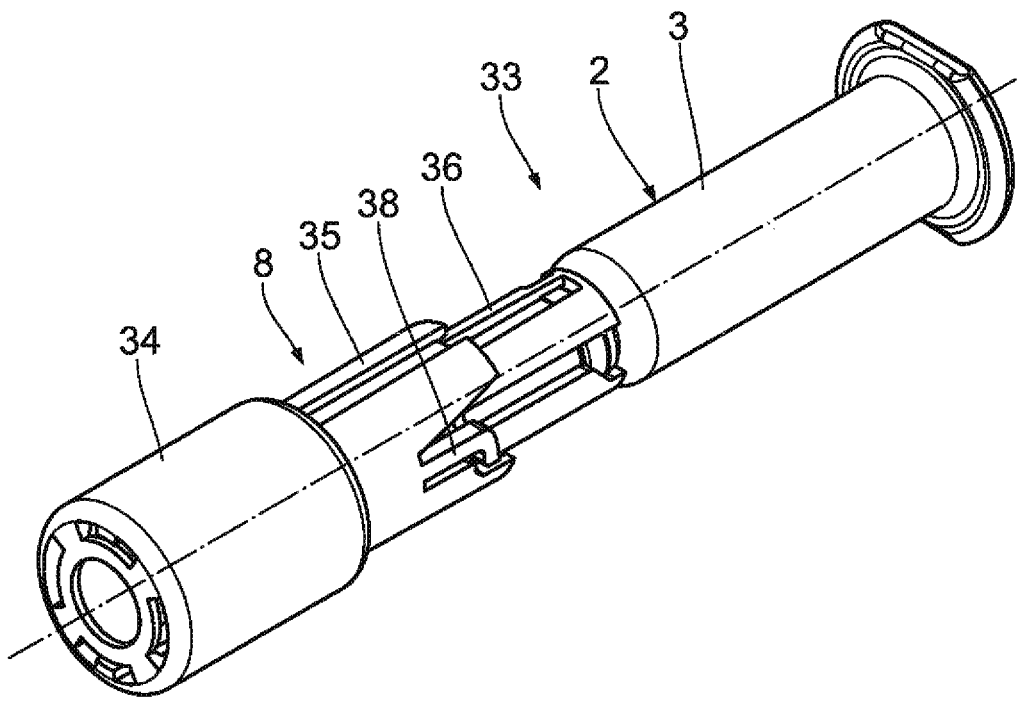
FIG. 14 shows the injection device according to FIG. 12 with its anti-puncture device in the protection position.
Figure 16:
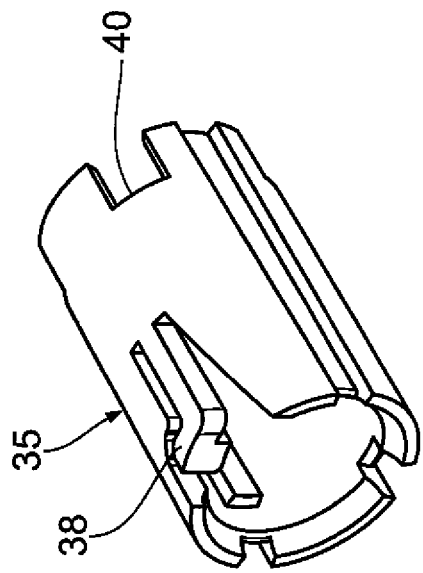
FIG. 16 shows a telescopic sleeve of the anti-puncture device according to FIGS. 12 to 14 which is arranged between the positive-fit adapter according to FIG. 15 and a telescopic protection sleeve of the anti-puncture device.
Figure 17:
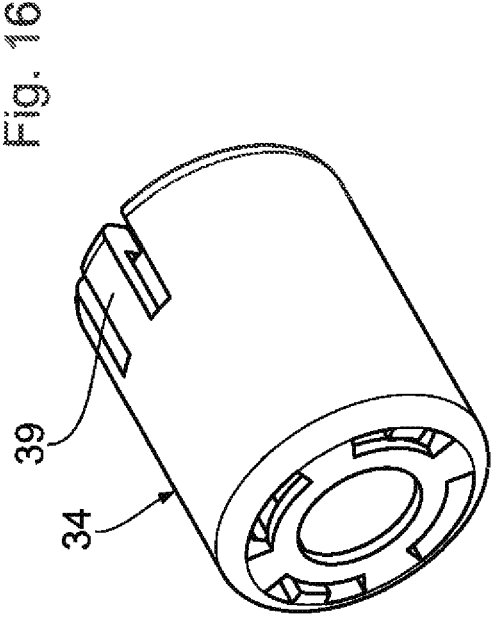
FIG. 17 shows the telescopic protection sleeve of the anti-puncture device according to FIGS. 12 to 14.

Upon assembly, the injection device 1 comprising the anti-puncture device 8 is in the injection position, and the protective cap 5, which had already been mounted, covers the injection needle 4 as shown in FIGS. 1 and 11. The various anti-rotation components ensure that the four components 10 to 13 of the anti-puncture device 8 are secured against rotation relative to each other and that the entire anti-puncture device 8 is secured against rotation relative to the injection device 2.

The injection device 1 is used as follows: In a first step, the protective cap 5 is removed from, in other words screwed off the injection cannula 4 (cf arrow 30 in FIG. 1). When the protective cap 5 is being screwed off, the cross-sectional design of the telescopic protection sleeve 10, which protrudes beyond the outer periphery of the container 3, ensures that in order to remove the protective cap 5, the user must grasp the injection device 1 by its telescopic protection sleeve 10. To this end, the telescopic protection sleeve 10 is provided with axially extending longitudinal ribs which prevent an unwanted movement of the telescopic protection sleeve 10 between the fingers of the user when removing the protective cap 5. Since all components of the anti-puncture device 8 are secured against rotation relative to each other, and the positive-fit adapter 13 is secured against rotation relative to the opening portion 6, it is ensured that when the protective cap 5 is rotated relative to the anti-puncture device 8 in the direction of the arrow 30 (or in a counter-direction thereto), the protective cap 5 is actually screwed off the opening portion 6 as required. When the protective cap 5 has been screwed off, it can be removed from the injection cannula 4.

Figure 2:
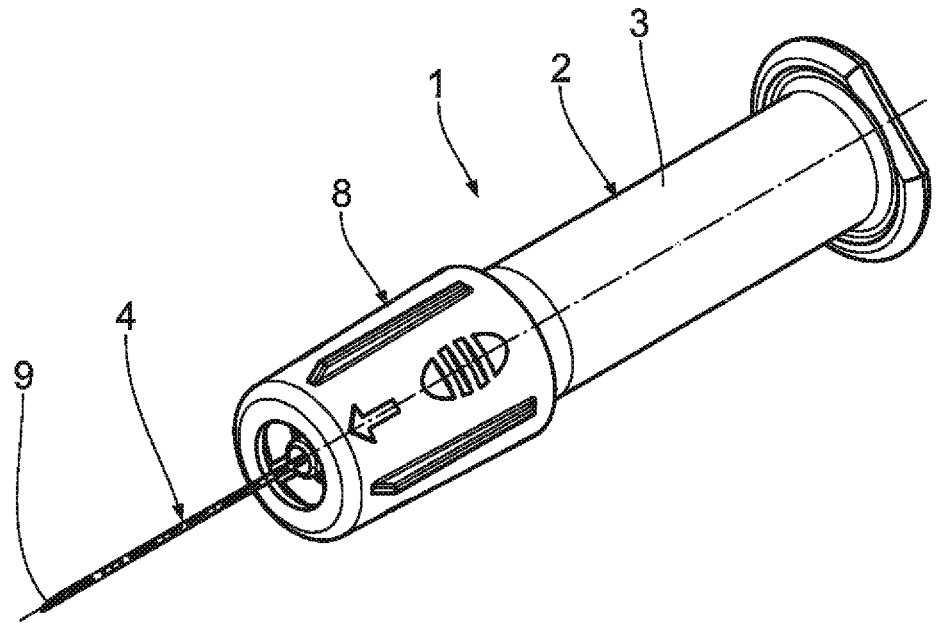
FIG. 2 shows the injection device according to FIG. 1 in a ready-to-use condition in which an original protective cap has been removed from an injection cannula.
Figure 3:
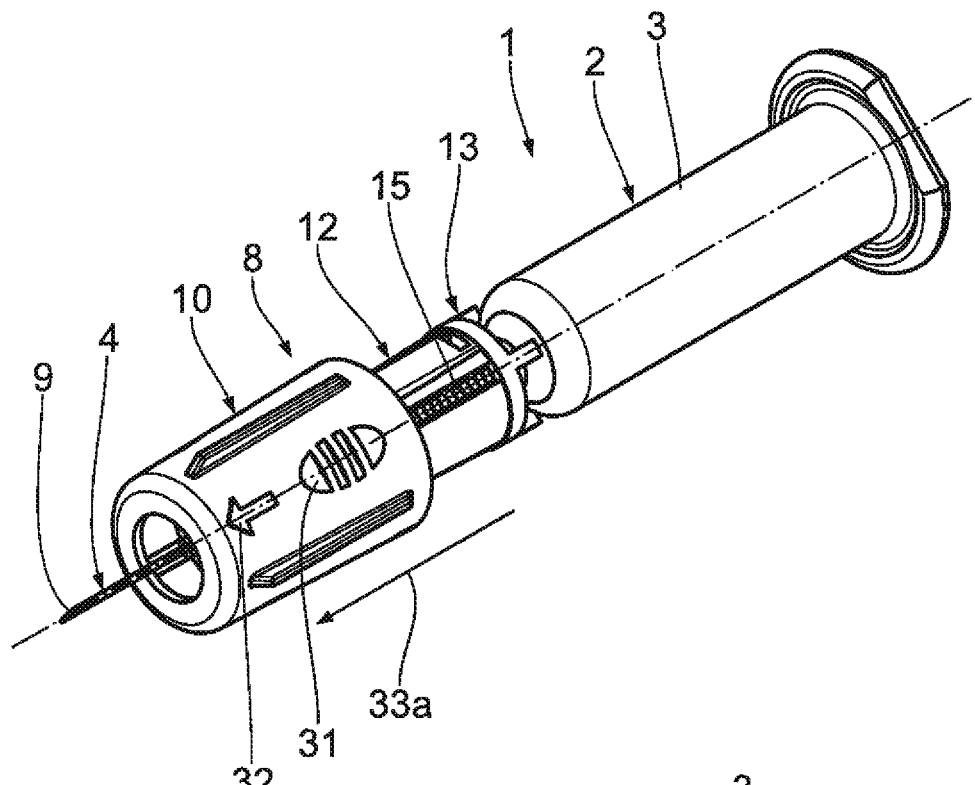
FIG. 3 shows the injection device according to FIG. 2 during a displacement of the telescopic anti-puncture device between an injection position according to FIGS. 1 and 2 in which the injection cannula is exposable (FIG. 1) or exposed (FIG. 2) for injection of a medium, and a protection position in which a cannula tip of the injection cannula is retracted into a protective component of the telescopic anti-puncture device.
Figure 4:
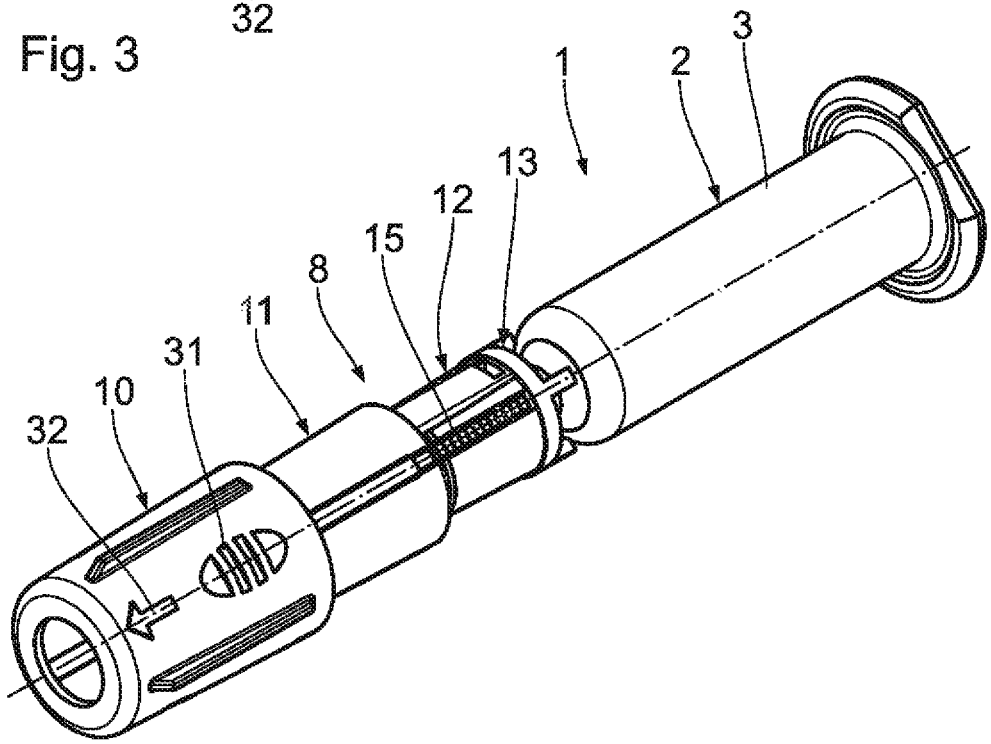
FIG. 4 shows the injection device comprising the telescopic anti-puncture device in the protection position.

The injection device 1 is now ready to use, which is shown in FIG. 2. In order to move the anti-puncture device 8 into the protection position (cf. FIGS. 3 to 7), a defined amount of pressure is applied to the telescopic protection sleeve 10 from both sides in a pressure region 31 marked on the outer telescopic protection sleeve 10. This causes the counter snap-in locking bodies 17 to disengage from the snap-in locking hooks 24, thus allowing the outer telescopic protection sleeve 10 to be axially extended relative to the telescopic sleeve 11 in the direction of the arrow 32 applied to the outer telescopic protection sleeve 10 (cf. arrow 33*a* in FIG. 3). In doing so, the counter snap-in locking body 17 clicks over the snap-in locking teeth 16 of the protective snap-in locking arrangement 14 until the end position of the counter snap-in locking body 17 in front of the near-end snap-in locking tooth 16' of the central telescopic sleeve 11 is reached. Afterwards, the central telescopic sleeve 11 is extended relative to the inner telescopic connection sleeve 12, causing the counter snap-in locking bodies 18 of the central telescopic sleeve 11 to click over the snap-in locking teeth 16 of the inner telescopic connection sleeve 12 until the end position of the counter snap-in locking body 18 is reached in which it abuts against the near-end snap-in locking tooth of the inner telescopic connection sleeve 12. The anti-puncture device 8 is now in the fully extended protection position according to FIG. 4. In this position, the cannula tip 9 of the injection cannula 4 is fully retracted into the telescopic protection sleeve 10, thus ensuring a secure anti-puncture protection. It shall be noted that due to the one-way design of the associated snap-in locking arrangements 14, it is not possible for a user to move the anti-puncture device 8 from the protection position according to FIG. 4 back to the state in which the cannula tip 9 is exposed without destroying it.

Another embodiment of an injection device 33 will hereinafter be explained with reference to FIGS. 12 to 17. Components and functions which correspond to those described above with reference to FIGS. 1 to 11 are designated by the same reference numerals and are not discussed in detail again.

The anti-puncture device 8 of the injection device 33 according to FIGS. 12 to 17 has three telescopic sleeves as well, namely an outer telescopic protection sleeve 34 the function of which corresponds to that of the telescopic protection sleeve 10 of the embodiment according to FIGS. 1 to 11, a central telescopic sleeve 35 the function of which corresponds to that of the telescopic sleeve 11 of the embodiment according to FIGS. 1 to 11, and an inner telescopic connection component 36 which is at the same time a positive-fit adapter for forming a positive fit between the anti-puncture device 8 and the injection device 2. In other words, the functions of the inner telescopic sleeve 12 and those of the positive-fit adapter 13 of the embodiment according to FIGS. 1 to 11 are combined in the telescopic connection component 36.

The telescopic connection component 36 is configured as a radially snap-lockable C-shaped adapter. The telescopic connection component 36 is radially snap-locked with the opening portion 6 of the container 3, causing the telescopic connection component 36 to engage a peripheral region of the snap-in locking collar 25 of the opening portion 6 in order to axially secure the telescopic connection component 36.

Figure 15:
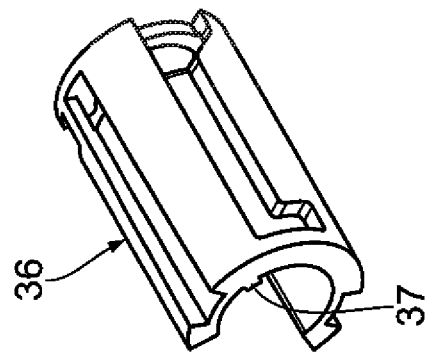
FIG. 15 shows a positive-fit adapter for forming a positive fit between the anti-puncture device according to FIGS. 12 to 14 and the injection unit, wherein the positive-fit adapter is configured as a C-shaped adapter that is radially snap-lockable thereto.
Figure 18:
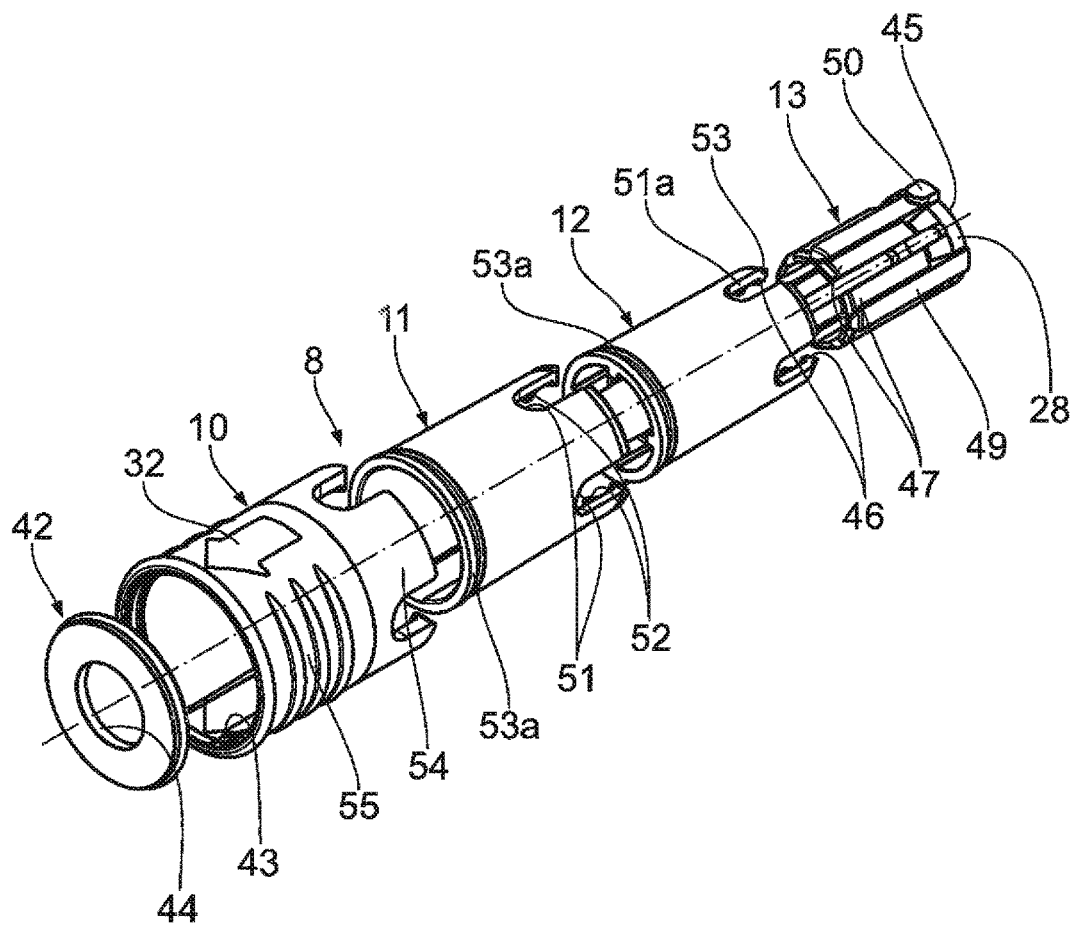
FIG. 18 shows an exploded view of another embodiment of a telescopic anti-puncture device for a medical injection device.
Figure 19:
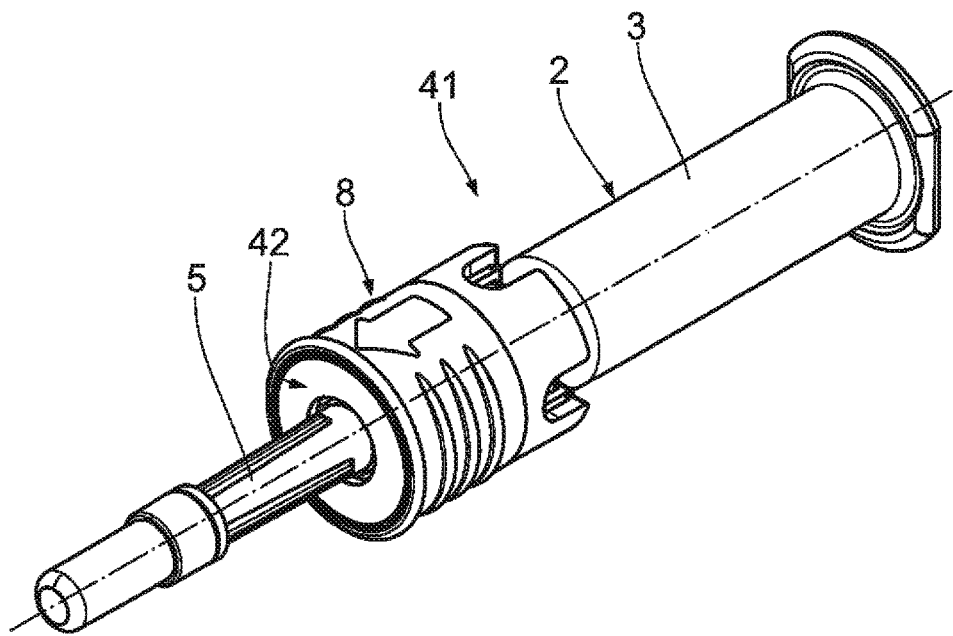
FIG. 19 shows an injection device comprising the anti-puncture device according to FIG. 18 in the injection position.
Figure 20:
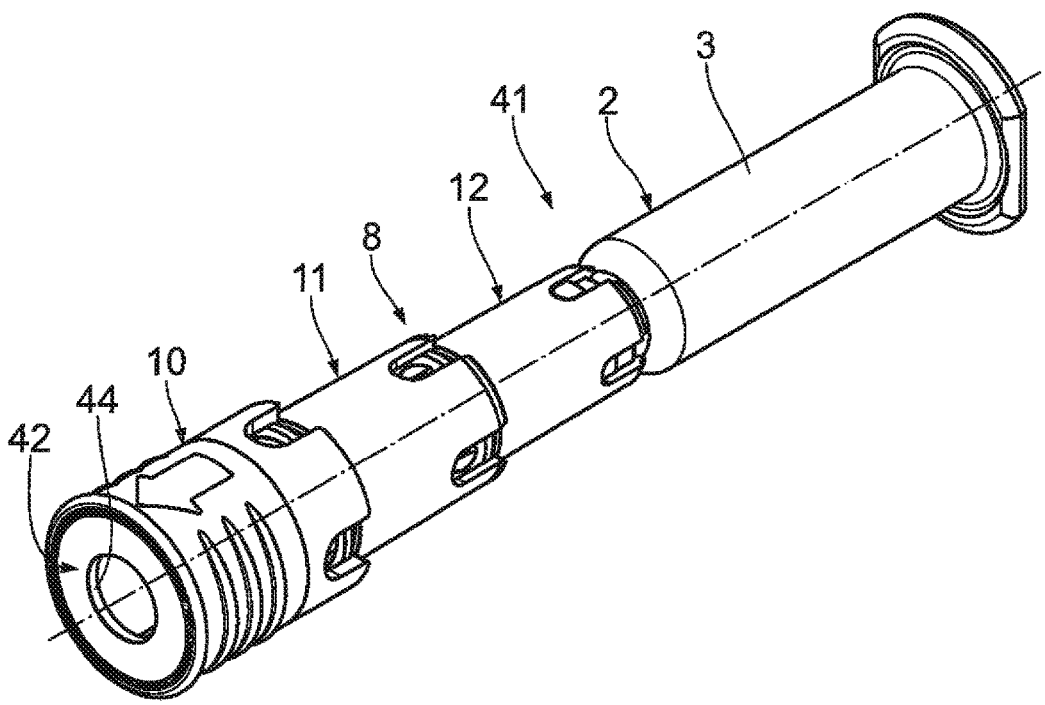
FIG. 20 shows the injection device according to FIG. 18 with its anti-puncture device in the protection position.
Figure 23:
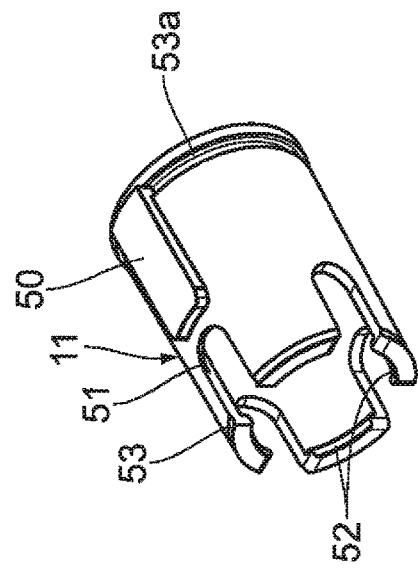
FIG. 23 shows a central telescopic sleeve of the anti-puncture device according to FIGS. 18 to 20 which is arranged between the telescopic connection sleeve according to FIG. 22 and a telescopic protection sleeve of the anti-puncture device.
Figure 24:
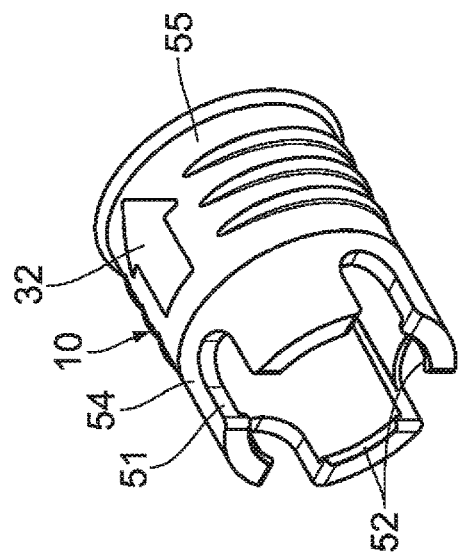
FIG. 24 shows the telescopic protection sleeve of the anti-puncture device according to FIGS. 18 to 20.
Figure 21:
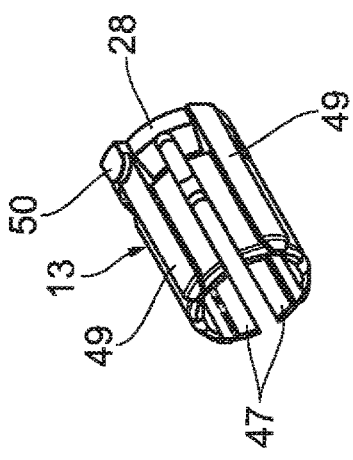
FIG. 21 shows a positive-fit adapter for forming a positive connection between the anti-puncture device according to FIGS. 18 to 20 and the injection unit.
Figure 22:
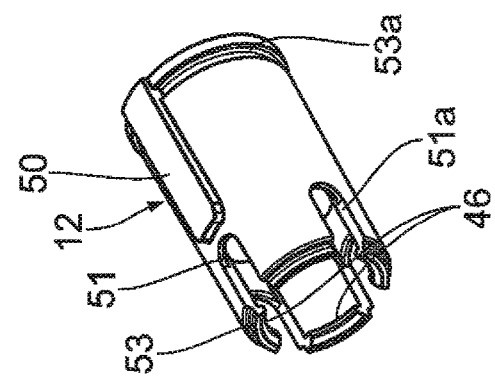
FIG. 22 shows a telescopic connection sleeve of the anti-puncture device according to FIGS. 18 to 20 which is arranged between the positive-fit adapter according to FIG. 12 and a central telescopic sleeve of the anti-puncture device.
Figure 25:
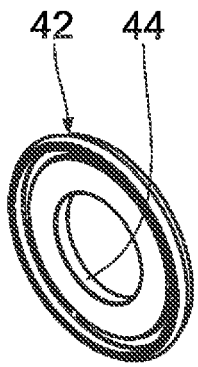
FIG. 25 shows an annular lid for the telescopic protection sleeve according to FIG. 24.
Figure 26:
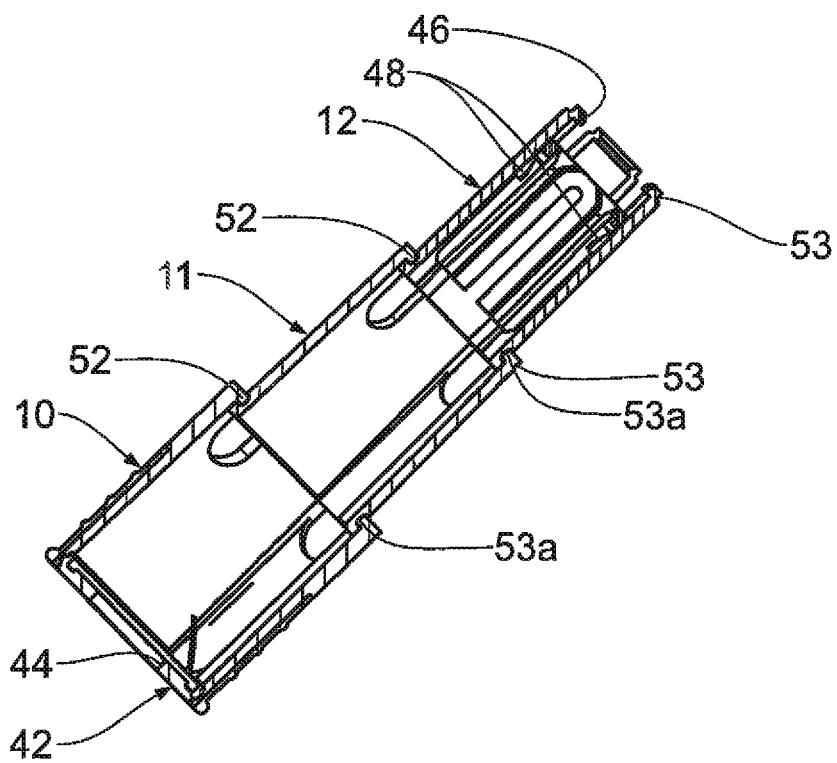
FIG. 26 shows an axial longitudinal section through the anti-puncture device according to FIGS. 18 to 20 shown in the protection position.
Figure 27:
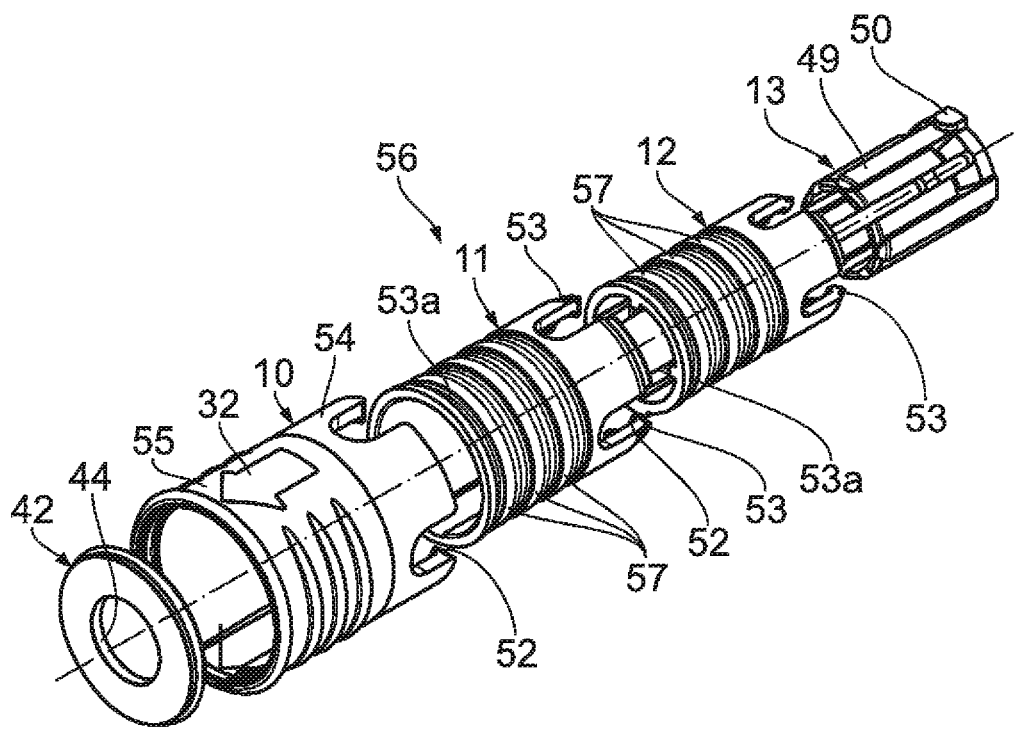
FIGS. 27 to 35 show illustrations, similar to FIGS. 18 to 26, of components of another embodiment of an anti-puncture device for an injection unit.
Figure 28:
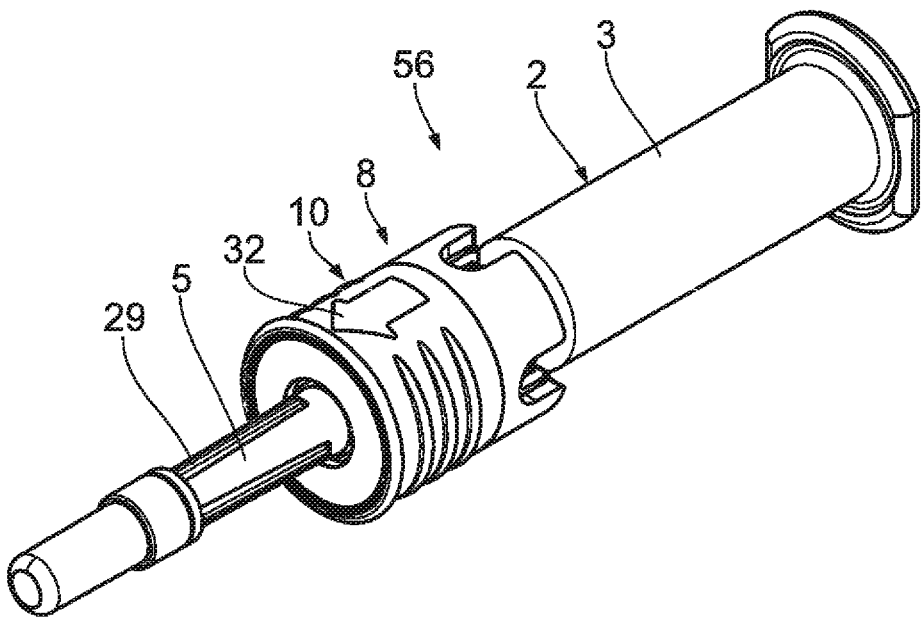
Figure 29:
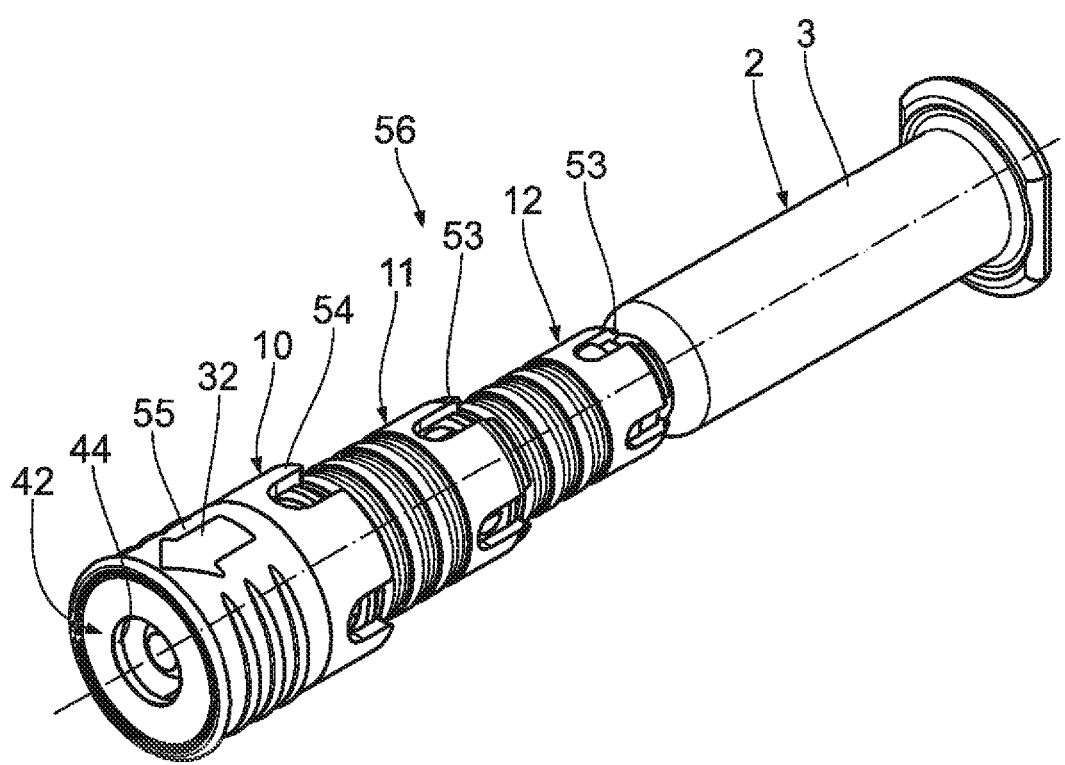
Figure 32:
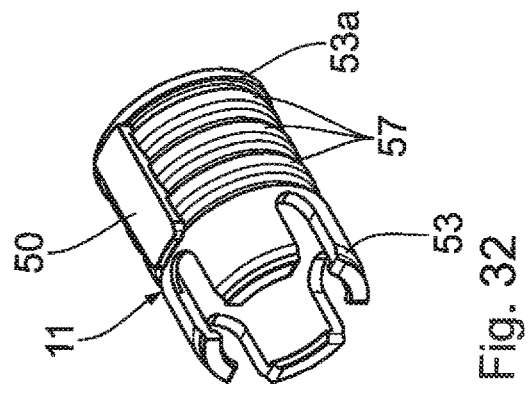
Figure 33:
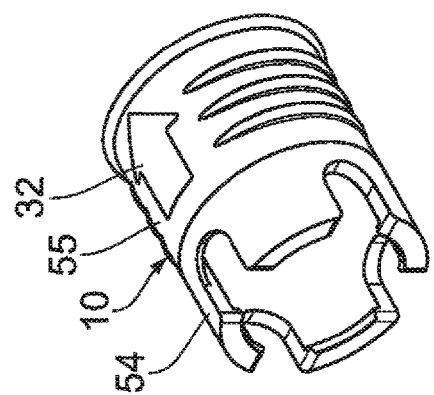
Figure 30:
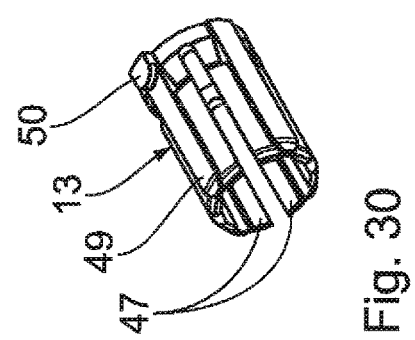
Figure 31:
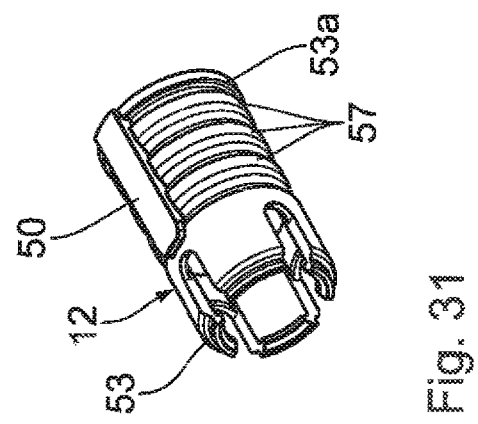
Figure 34:
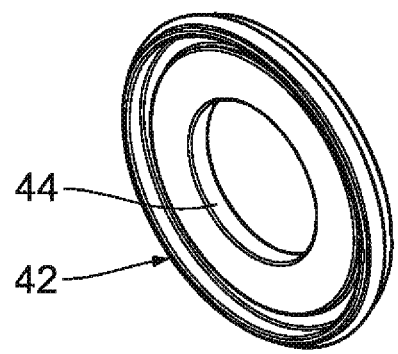
Figure 35:
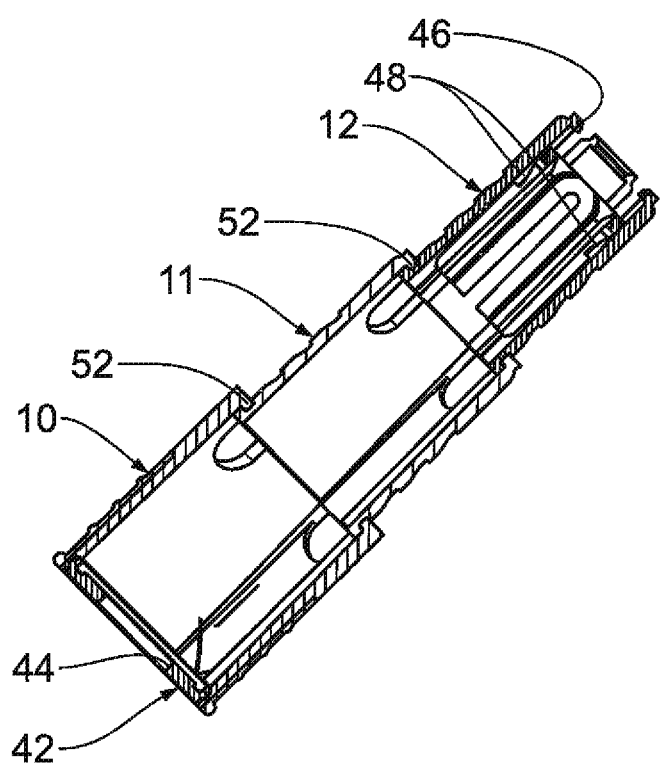
Figure 36:
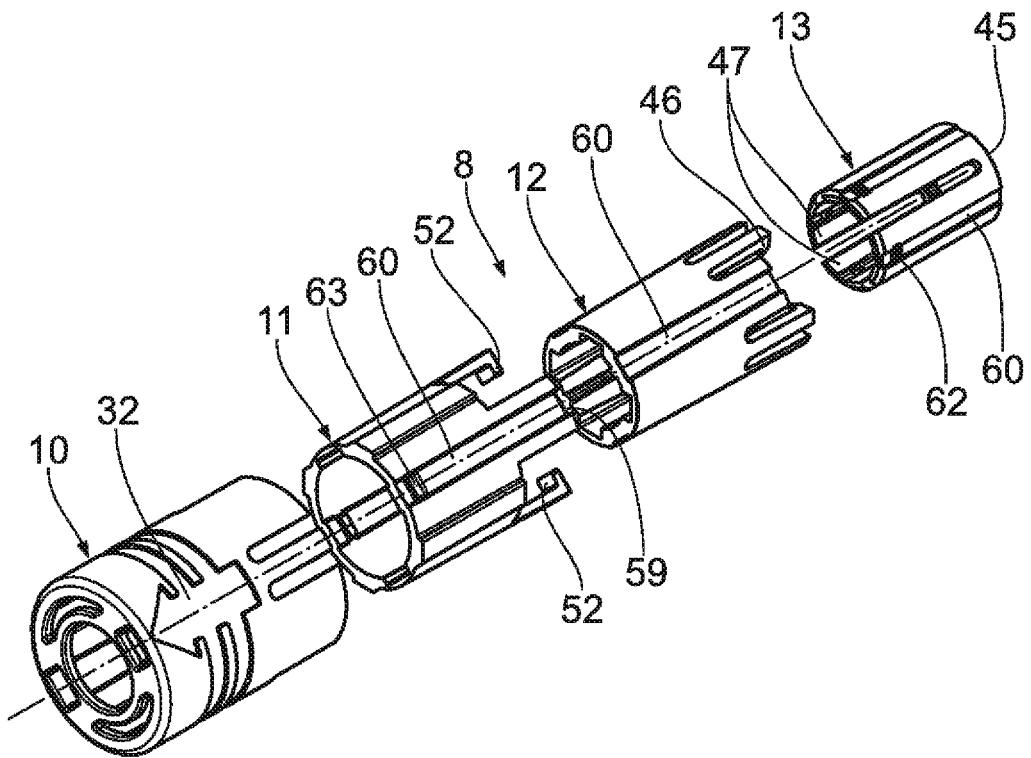
Figure 37:
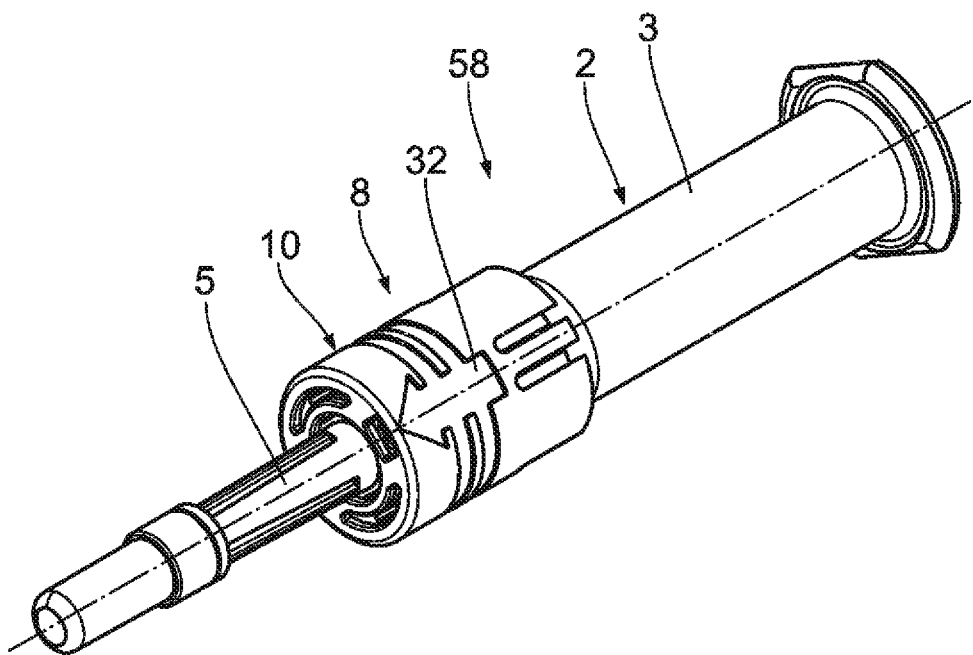
Figure 38:
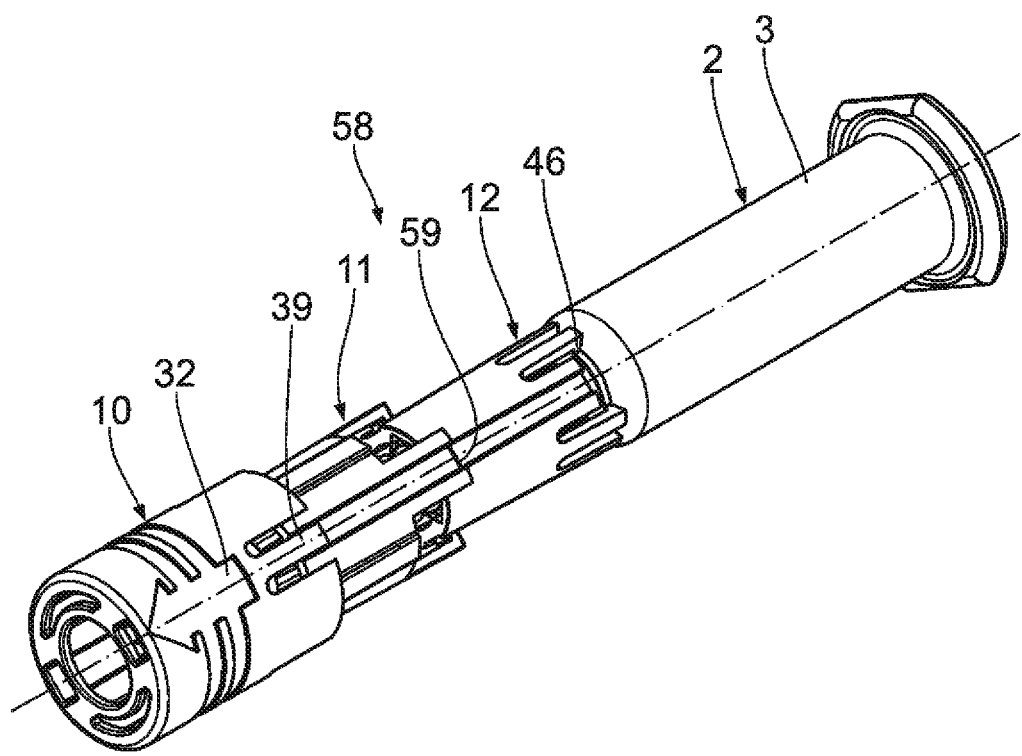
Figure 43:
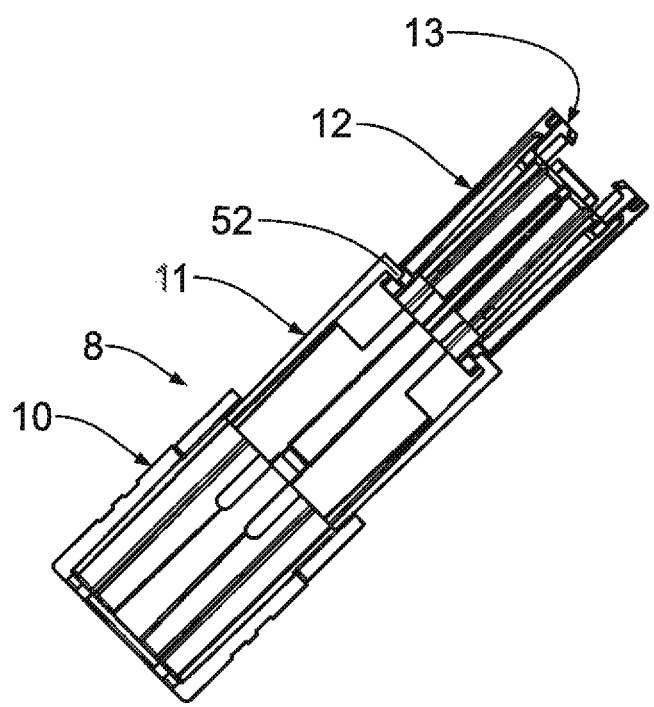
FIG. 43 shows an axial longitudinal section through the anti-puncture device according to FIGS. 36 to 38 shown in the protection position.

In order to increase the frictional fit between the telescopic connection component 36 and the opening portion 6 of the container 3 of the injection unit 2, and therefore in particular to ensure an anti-rotation protection, inner ribs 37 of the telescopic connection component 36, which—in the assembled state—abut against the opening portion 6 between the peripheral ribs 29 thereof, are made of a softer plastic material than the rest of the base body of the telescopic connection component 36. The ribs 37 may for example be formed on the base body of the telescopic connection component 36 by multi-component technology, in particular by 2C technology. FIG. 15 shows only one rib 37 of the inner ribs 37. The base body is however provided with more than one, for instance five, ribs 37 which are arranged at equal distances from each other when seen in the peripheral direction, wherein this distance is adapted to the peripheral distance of the peripheral ribs 29.

The central telescopic sleeve 35 (cf. FIG. 16) is connected to the telescopic connection component 36 via a radially acting snap-in locking connection. To this end, the central telescopic sleeve 35 is provided with a flexible tongue 38 which engages into a corresponding snap-in locking recess of the telescopic connection component 36.

The outer telescopic protection sleeve 34 is provided with a flexible tongue 39 as well which engages with a rear side of a corresponding snap-in locking receptacle in the central telescopic sleeve 35 or in the telescopic connection arrangement 36 so as to form a locking connection. The flexible tongue 39 and the snap-in locking receptacle associated therewith in the injection position thus combine to form the injection connection arrangement for positively securing the telescopic protection sleeve 34 to the injection unit 2 in the injection position.

In the protection position of the anti-puncture device 8 in the embodiment according to FIGS. 12 to 17, the snap-in latch 39 engages with a rear side of a snap-in receptacle 40 which is formed in the central telescopic sleeve 35. As a result, a protective snap-in locking arrangement is obtained which, together with a corresponding snap-in locking connection between the central telescopic sleeve 35 and the telescopic connection component 36, ensures that the telescopic protection sleeve 34 is securely held in place in the protection position.

Apart from the differences explained above, assembly and usage of the injection device 33 correspond to the above description of the injection device 1.

Another embodiment of an injection device 41 will be explained below with reference to FIGS. 18 to 26. Components and functions which correspond to those that have already been described above with reference to the injection devices 1 and 33 are designated by the same reference numerals and are not discussed in detail again.

The injection device 41 is provided with a telescopic anti-puncture device 8 as well which comprises a telescopic connection sleeve 12, a positive-fit adapter 13, a central telescopic sleeve 11 and a telescopic protection sleeve 10 and therefore has basically the same structure as the protective device 8 of the injection device 1. There are however differences in the structures of the snap-in locking connections and of the guide systems. In the injection device 41, the snap-in locking connections are configured as axial snap-in locking connections.

In the anti-puncture device 8 of the injection device 41, the telescopic protection sleeve 10 is composed of two parts, thus consisting of the actual telescopic sleeve and an additional ring-shaped lid 42. An outer periphery of the lid 42 is snap-locked with an inner peripheral groove 34 in an outer end region of the telescopic protection sleeve 10. An outer periphery of the lid 42 combines with the inner peripheral groove 43 to form an annular snap fit between the lid 42 and the telescopic protection sleeve 10. The lid 42 is provided in order to reduce an externally accessible opening width of the telescopic protection sleeve 10 to such an extent that a through-opening 44 is obtained which has a diameter that is smaller than the internal diameter of the remaining telescopic protection sleeve 10.

During assembly of the anti-puncture device 8 according to FIGS. 18 to 26, the central telescopic sleeve 11 is at first inserted into the telescopic protection sleeve 10 from the side; at this point, the telescopic protection sleeve 10 is not yet provided with a lid 10. Afterwards, the telescopic connection sleeve 12 is inserted into the central telescopic sleeve 11 from the same side. Then the lid 42 is snap-locked with the inner peripheral groove 43. Finally, the positive-fit adapter 13 is inserted into the telescopic connection sleeve 12 from the opposite side.

The anti-puncture device preassembled in this manner is then ready to be push-fitted onto the injection unit 2. This is done until a stop collar 45 of the positive-fit adapter 13 abuts against the snap-in locking collar 25 of the injection unit 2 (cf. for instance FIG. 8).

When the anti-puncture device 8 according to FIGS. 18 to 26 is moved further along the injection unit 2 in the direction of the container 3, the telescopic connection sleeve 12 is axially displaced in the direction of the positive-fit adapter 13, which is then axially secured to the snap-in locking collar 25, until snap-in locking hooks 46 formed on the telescopic connection sleeve 12 engage the snap-in locking collar 25 of the opening portion 6 of the injection unit 2. In the injection device 41, the positive connection in the injection position between the telescopic protection sleeve 10 in its function as protective component of the anti-puncture device 8 as well as other components thereof and the injection unit 2 is not achieved by means of snap-in locking hooks provided at the positive-fit adapter 13 but by means of the snap-in locking hooks 46 provided at the telescopic connection sleeve instead.

In the injection device 41, an anti-rotation protection is provided between the anti-puncture device 8, which is at the same time an anti-rotation device, and the opening portion 6 of the injection unit 2 as well. To this end, the positive-fit adapter 13 of the injection device 41 is again provided with anti-rotation latches 47 which correspond to the snap-in latches 27 of the embodiment according to FIGS. 1 to 11. The anti-rotation latches 47 extend axially and are interconnected via the carrier ring 28 of the positive-fit adapter 13 of the injection device 41. In the assembled state, the anti-rotation latches 27 are in each case received between two adjacent, axially extending peripheral ribs 29 of the opening portion 6 of the injection unit 2.

The anti-rotation latches 27 are held between the peripheral ribs 29 by means of a hold-down means formed on the telescopic connection sleeve 12. Said hold-down means is formed by a total of four inner axial ribs two of which are visible in the axial sectional view according to FIG. 26. Seen in the peripheral direction, the axial ribs 48 are formed on an inner wall of the telescopic connection sleeve 12 in such a way as to be staggered relative to each other by in each case 90°. Each of the axial ribs 48 interacts with a counter hold-down means at the positive-fit adapter 13 in order to hold down in each case one anti-rotation latch 47. The counter hold-down means are formed by outer axial ribs 49 at the positive-fit adapter 13. (cf. FIG. 21).

The positive-fit adapter 13 is secured to the telescopic connection sleeve 12 while in each case two telescopic sleeves 12, 11, 10 abutting against each other are secured relative to each other by means of anti-rotation devices so as to prevent a relative rotation thereof about the longitudinal axis of the anti-puncture device 8. Said anti-rotation device is again formed by outer tongues 50 at in each case one of the components 13, 12, 11 which interact with complementary inner axial grooves 51 in the respective adjacent telescopic sleeves 12, 11, 10 in such a way as to prevent rotation.

At the same time, the tongues 50 act as stops which interact, via the snap-in locking hooks 46 of the telescopic connection sleeve 12, with axially extending recesses 51a acting as stops defining an axial end position of the telescopic connection sleeve 12 relative to the positive-fit adapter 13 when the anti-puncture device 8 is snap-locked with the snap-in locking collar 25 of the opening portion 6.

The central telescopic sleeve 11 and the telescopic protection sleeve 10 are also provided with radially acting snap-in locking hooks 52 which are comparable to the snap-in locking hooks 46 of the telescopic connection sleeve 12. Just like the snap-in locking hooks 46, the snap-in locking hooks 52 are also arranged in such a way as to be staggered relative to each other by 90° when seen in the peripheral direction. In the injection position, for instance according to FIG. 19, the snap-in locking hooks 46, 52 of adjacent telescopic sleeves 12, 11, 10 are arranged one above the other in such a way as to be in perfect alignment. The snap-in locking hooks 52 of the central telescopic sleeve 11 engage complementary recesses 53 in the outside of the snap-in locking hooks 46. The snap-in locking hooks 52 of the telescopic protection sleeve 10 engage corresponding recesses 53 in the outside of the snap-in locking hooks 52 of the central telescopic sleeve 11.

In the protection position of the anti-puncture device 8 (cf for instance FIGS. 20 and 26), the snap-in locking hooks 52 of the central telescopic sleeve 11 on the one hand and of the telescopic protection sleeve 10 on the other interact with outer peripheral grooves 53a formed in the telescopic connection sleeve 12 on the one hand and in the central telescopic sleeve 11 on the other.

When the telescopic sleeves 11, 10 are moved from the retracted injection position to the extended protection position, the snap-in locking hooks 52 slide between the respective counter recesses 53 and the peripheral grooves 53a. In order to ensure that an even force is applied to the snap-in locking hooks 52 when the telescopic sleeves 11, 10 are being moved to the protective position, the telescopic sleeves 12, 11 widen conically between the respective counter recesses 53 and the respective peripheral grooves 53a.

The telescopic protection sleeve 10 is configured as a 2C (two component) injection-molded part. The telescopic protection sleeve 10 includes a carrier body 54 as well as a grip portion 55. The carrier body 54 on the one hand and the grip portion 55 on the other are configured as different injection-molded components of the 2C component. Suitable 2C plastic materials include for example ABS (acrylonitrile budadiene styrene) for a hard component such as the carrier body 54, and TPE (thermoplastic elastomer) for a soft component such as the grip portion 55. It is conceivable as well to use a different number of components for a multi-component injection-molded part of this type, for instance three or more components made of different plastic materials of an in particular different hardness.

Being configured as a 2C (two component) injection-molded part, the telescopic protection sleeve 10 ensures a more secure grip in the region of the grip portion 55 of the telescopic protection sleeve 10.

The axial ribs 48 of the telescopic connection sleeve 12 may also be formed of a plastic material which is different from that of the remaining telescopic connection sleeve 12, and the axial ribs 48 may be secured to a carrier body of the telescopic connection sleeve 12 by means of 2C injection molding technology.

Another embodiment of the injection device 56 will be explained below with reference to FIGS. 27 to 35. Components and functions which correspond to those described above with reference to the injection devices 1, 33 and 41 and in particular with reference to the injection device 41 are designated by the same reference numerals and are not discussed in detail again.

The telescopic connection sleeve 12 and the central telescopic sleeve 11 are in each case provided with three intermediate notches 57 between the counter recesses 53 and the peripheral grooves 53a. When the telescopic protection sleeve 10 and the central telescopic sleeve 11 are displaced from the injection position into the protection position, the respective snap-in locking hooks 52 of the telescopic protection sleeve 10 and those of the central telescopic sleeve 11 click over the intermediate notches 57 along their displacement path between the respective counter recesses 53 and the respective peripheral grooves 53a. As a result, a haptic feedback is delivered to the user informing him about the distance already covered by the two telescopic sleeves 10, 11 on their way between the injection position and the protection position.

Another embodiment of an injection device 58 will be explained below with reference to FIGS. 36 to 43. Components and functions which correspond to those described above with reference to the injection devices 1, 33, 41 and 56 are designated by the same reference numerals and are not discussed in detail again.

Similar to the injection device 1, the injection device 58 is composed of four parts as well, thus comprising an inner positive-fit adapter 13, a telescopic connection sleeve 12, a central telescopic sleeve 11 and an outer telescopic protection sleeve 10.

The function of snap-in locking hooks 46 and 52 of the telescopic sleeves 12, 11 and 10 of the injection device 58 is similar to that of the injection device 41. The telescopic sleeves 11 and 10 are in each case provided with two snap-in locking hooks 52 which are arranged opposite to each other, in other words they are staggered relative to each other by 180° when seen in the peripheral direction. Similar to the concept of the counter snap-in locking bodies and the snap-in locking teeth in the injection device 1, the snap-in locking hooks 52 of the central telescopic sleeve 11 are staggered relative to the snap-in locking hooks 52 of the telescopic protection sleeve 10 by 90° in the peripheral direction when the injection device 8 is mounted. During assembly, the central telescopic sleeve 11 is at first inserted into the outer telescopic protection sleeve 10 in the direction of the arrow 32 until the snap-in locking hooks 52 of the outer telescopic protection sleeve 10 engage counter recesses 59 of the central telescopic sleeve 11 which are formed at the end of axial guideways 60 in an outer wall of the central telescopic sleeve 11.

Afterwards the telescopic connection sleeve 12 is inserted into the central telescopic sleeve 11 in the direction of the arrow 32 as well. This is done until the snap-in locking hooks 52 of the central telescopic sleeve 11 engage recesses 61 of the telescopic connection sleeve 12 which are in turn formed at the end of axial guideways 60 in an outer wall of the telescopic connection sleeve 12.

In the next step, the positive-fit adapter 13 is inserted into the telescopic connection sleeve 12 in the direction of the arrow 32 as well until the snap-in locking hooks 46 of the telescopic connection sleeve 12 engage recesses 62 of the positive-fit adapter 13 from outside. The recesses 62 are again formed in axial guideways 60 of the positive-fit adapter 13. In the position preassembled in this manner, the sleeves 11 and 12 are virtually completely arranged in the outer telescopic protection sleeve 10. The largest part of an axial extension of the positive-fit adapter 13 between the recesses 62 and the stop collar 45 protrudes beyond the telescopic sleeves 10 to 12 inserted into each other.

When the preassembled anti-puncture device 8 is to be mounted to the injection device 2, the anti-puncture device 8 is push-fitted onto the opening portion 6 of the injection unit 2 with the positive-fit adapter 13 going in first until the stop collar 45 abuts against the snap-in locking collar 25 of the opening portion 6. Afterwards the three telescopic sleeves 10 to 12 inserted into each other are moved axially in the direction of the container 3, causing the snap-in locking hooks 46 of the telescopic connection sleeve 12 to disengage from the recesses 62 of the positive-fit adapter 13 so as to slide along the guideways 60 before engaging the snap-in locking collar 25 in order to secure the anti-puncture device 8 to the injection unit 2. At the same time, another set of hold-down means ensure that the anti-rotation latches 47 of the positive-fit adapter 13 between adjacent peripheral ribs 29 of the opening portion 6 are held down in order to prevent a rotation of the anti-puncture device 8 relative to the injection unit 2.

The interaction of the guideways 60 with the associated snap-in locking hooks 46, 52 prevents rotation of the components of the anti-puncture device 8 relative to each other. Axial guideways, which are arranged at an angle of 90° relative to the structure of snap-in locking hooks and guideways, provide an additional amount of anti-rotation protection.

The anti-puncture device 8 is now ready to use in the injection position.

When the anti-puncture device 8 is moved from the injection position into the protection position, the snap-in locking hooks 52 of the central telescopic sleeve 11 disengage from the recesses 61 of the telescopic connection sleeve 12 while the snap-in locking hooks 52 of the outer telescopic protection sleeve 10 disengage from the counter recesses 59 of the central telescopic sleeve 11. The snap-in locking hooks of the telescopic sleeves 10, 11 move axially along the respective guideways 60 of the telescopic sleeves 11 and 12 until the snap-in locking hooks 52 of the outer telescopic protection sleeve 10 engage recesses 63 which are formed at ends of the guideways 60 that are opposite to the counter recesses 59. In the protection position, the snap-in locking hooks 52 of the central telescopic sleeve 11 further engage recesses 63 which are formed at ends in the guideways 60 of the telescopic connection sleeve 12 that are opposite to the recesses 61. The anti-puncture device 8 is now in the extended protection position according to FIG. 38 or 43.

What is claimed is:

1. A medical injection device comprising:
   an injection unit including
      a container for a medium to be injected;
      a port and connection portion which is connected, via a plug-in connection, to a near-cannula end of the container; and
      an injection cannula which communicates with the container via the port and connection portion;
   a protective cap for the injection cannula which is detachably connected to the port and connection portion at a near-cannula end of the port and connection portion; and
   an anti-rotation device
      which is non-rotationally connected to the port and connection portion; and
      which surrounds an outside of the port and connection portion in the manner of a sleeve;
   wherein the anti-rotation device is connected to the injection unit via a positive-fit adapter;
   wherein the positive-fit adapter is non-rotationally connected to the port and connection portion via a positive-fit connection; and
   wherein the positive-fit adapter is a component of the anti-rotation device, and
   wherein the anti-rotation device comprises
      at least one positive-fit latch which is part of the positive-fit adapter and which is received between two adjacent, axially extending peripheral ribs of the port and connection portion; and
      at least one hold-down means which holds the at least one positive-fit latch between the peripheral ribs.

2. The injection device according to claim 1, wherein the anti-rotation device axially covers the plug-in connection.

3. The injection device according to claim 1, wherein the at least one positive-fit latch is formed in one piece with a carrier ring of the positive-fit adapter, wherein the carrier ring is push-fittable onto the port and connection portion and is snap-locked therewith.

4. The injection device according to claim 1, wherein the at least one hold-down means has at least one inner axial rib which interacts with a counter hold-down means at the positive-fit adapter in order to hold down the at least one positive-fit latch.

5. The injection device according to claim 1, wherein at least one part of the anti-rotation device is configured as a multi-component injection-molded part.

6. The injection device according to claim 5, wherein different components of the at least one multi-component injection-molded part of the anti-rotation device are made of different plastic materials.

7. The injection device according to claim 6, wherein the different plastic materials have different hardnesses.

8. The injection device according to claim 5, wherein the at least one multi-component injection-molded part of the anti-rotation device is configured as an outer sleeve which has at least one grip portion and at least one carrier body, wherein the at least one carrier body and the at least one grip portion are configured as different injection-molded components of the at least one multi-component injection-molded part.

* * * * *